(12) United States Patent
Kim et al.

(10) Patent No.: US 12,138,352 B2
(45) Date of Patent: *Nov. 12, 2024

(54) NANOHELIX-SUBSTRATE COMPLEX FOR CONTROLLING MACROPHAGE BEHAVIOR, PREPARATION METHOD THEREOF, AND METHOD OF CONTROLLING ADHESION AND POLARIZATION OF MACROPHAGE BY USING THE SAME

(71) Applicant: Korea University Research and Business Foundation, Seoul (KR)

(72) Inventors: Young-Keun Kim, Seoul (KR); Heemin Kang, Seoul (KR); Min-Jun Ko, Seoul (KR); Gunhyu Bae, Hwaseong-si (KR)

(73) Assignee: Korea University Research and Business Foundation, Seoul (KR)

( * ) Notice: Subject to any disclaimer, the term of this patent is extended or adjusted under 35 U.S.C. 154(b) by 332 days.

This patent is subject to a terminal disclaimer.

(21) Appl. No.: 17/368,883

(22) Filed: Jul. 7, 2021

(65) Prior Publication Data
US 2022/0110880 A1   Apr. 14, 2022

(30) Foreign Application Priority Data
Oct. 13, 2020   (KR) .................. 10-2020-0131888

(51) Int. Cl.
| | | |
|---|---|---|
| *A61K 9/51* | (2006.01) | |
| *A61K 47/69* | (2017.01) | |
| *A61N 2/00* | (2006.01) | |
| *C12N 5/0786* | (2010.01) | |
| *C12N 13/00* | (2006.01) | |

(52) U.S. Cl.
CPC .......... *A61K 9/5115* (2013.01); *A61K 9/5123* (2013.01); *A61K 47/6929* (2017.08); *A61N 2/00* (2013.01); *C12N 5/0645* (2013.01); *C12N 13/00* (2013.01); *A61N 2/002* (2013.01)

(58) Field of Classification Search
CPC ........ A61N 2/00; A61N 2/002; C12N 5/0645; C12N 13/00
See application file for complete search history.

(56) References Cited

U.S. PATENT DOCUMENTS
2018/0327919 A1   11/2018   Kim et al.
2019/0102585 A1*   4/2019   Modiano .............. A61B 5/6852

FOREIGN PATENT DOCUMENTS
KR   10-1916588 B1   11/2018

OTHER PUBLICATIONS

Sitasuwan, P., "RGD-conjugated rod-like viral nanoparticles on 2D scaffold improve bone differentiation of mesenchymal stem cells," Frontiers in Chemistry 2: 31. doi: 10.3389/fchem.2014.00031. eCollection 2014. (Year: 2014).*
Banderas, A. I. M., M.S. Thesis: A Combined Chemical and Magneto-Mechanical Induction of Cancer Cell Death by the Use of Functionalized Magnetic Iron Nanowires (King Abdullah University of Science and Technology; Apr. 11, 2016) (Year: 2016).*
Mero, A., et al., "Covalent conjugation of poly(ethylene glycol) to proteins and peptides: strategies and methods," Methods Mol Biol 751: 95-129. doi: 10.1007/978-1-61779-151-2_8. (Year: 2011).*
Extended European Search Report issued on Jan. 19, 2022, in counterpart European Patent Application No. 21189669.1; (9 pages in English).
Min, Sunhong, et al. "Remote Control of Time-Regulated Stretching of Ligand-Presenting Nanocoils In Situ Regulates the Cyclic Adhesion and Differentiation of Stem Cells." *Advanced Materials* 33.11 (Feb. 2, 2021): 2008353; (9 pages in English).
Bae, Gunhyu, et al. "Immunoregulation of macrophages by controlling winding and unwinding of nanohelical ligands." *Advanced Functional Materials* 31.37 (Jun. 18, 2021): 2103409.; (16 pages in English).
Choi, Hyojun, et al. "Remote Manipulation of Slidable Nano-Ligand Switch Regulates the Adhesion and Regenerative Polarization of Macrophages." *Advanced Functional Materials* 30.35 (Jul. 9, 2020): 2001446.; (13 pages in English).
Min, Sunhong, et al. "Independent Tuning of Nano-Ligand Frequency and Sequences Regulates the Adhesion and Differentiation of Stem Cells." *Advanced Materials* 32.40 (Aug. 20, 2020): 2004300.; (8 pages in English).
Khatua, Chandra, et al. "In Situ Magnetic Control of Macroscale Nanoligand Density Regulates the Adhesion and Differentiation of Stem Cells." *Nano letters* 20.6 (May 14, 2020): 4188-4196.; (9 pages in English).
Wong, Dexter SH, et al. "Magnetically tuning tether mobility of integrin ligand regulates adhesion, spreading, and differentiation of stem cells." *Nano letters* 17.3 (Feb. 14, 2017): 1685-1695.; (11 pages in English).
Kang, Heemin, et al. "Magnetic manipulation of reversible nanocaging controls in vivo adhesion and polarization of macrophages." *ACS nano* 12.6 (May 16, 2018): 5978-5994. ; (17 pages in English).

* cited by examiner

*Primary Examiner* — Tracy Vivlemore
*Assistant Examiner* — Eric J Rogers
(74) *Attorney, Agent, or Firm* — NSIP Law

(57) ABSTRACT

The present invention relates to a nanohelix-substrate complex for controlling adhesion and polarization of macrophages, a manufacturing method thereof, and a method of controlling adhesion and polarization of macrophages by using the nanohelix-substrate complex, and the method of controlling adhesion and polarization of macrophages may temporally and reversibly control adhesion and phenotypic polarization of macrophages in vivo and ex vivo by controlling application/non-application of a magnetic field to the nanohelix-substrate complex.

12 Claims, 23 Drawing Sheets
(12 of 23 Drawing Sheet(s) Filed in Color)

[FIG. 1]
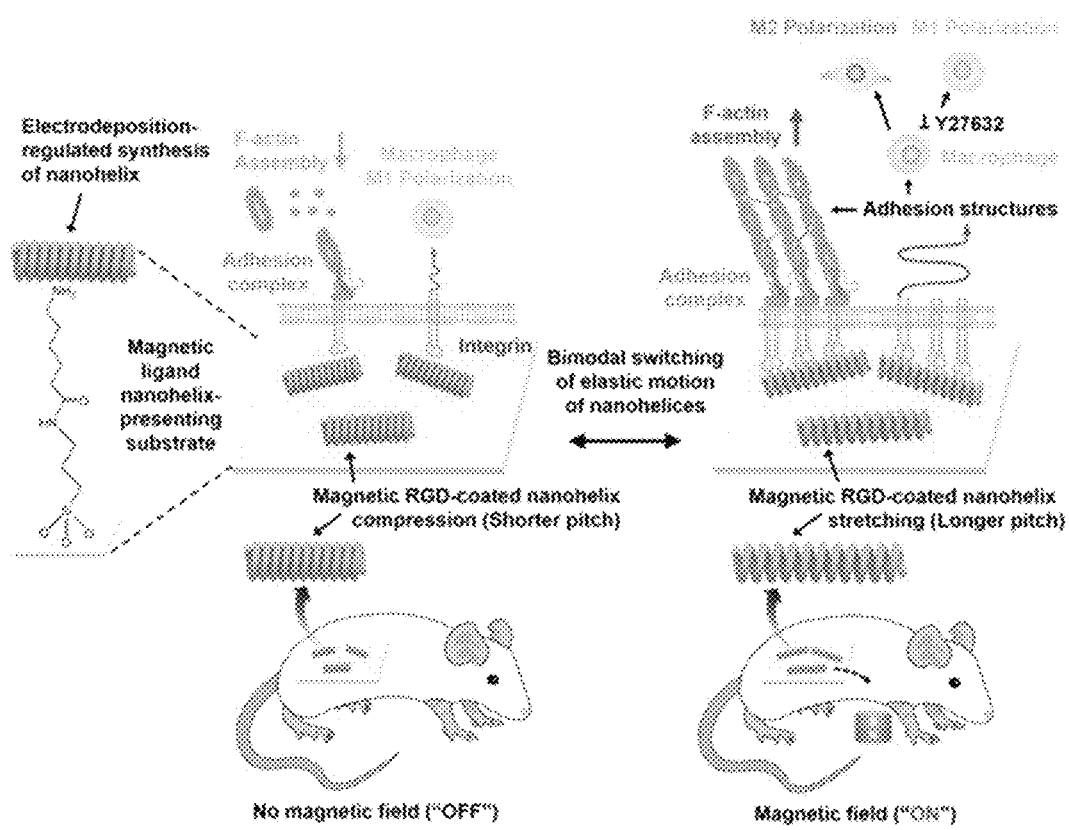

[FIG. 2]
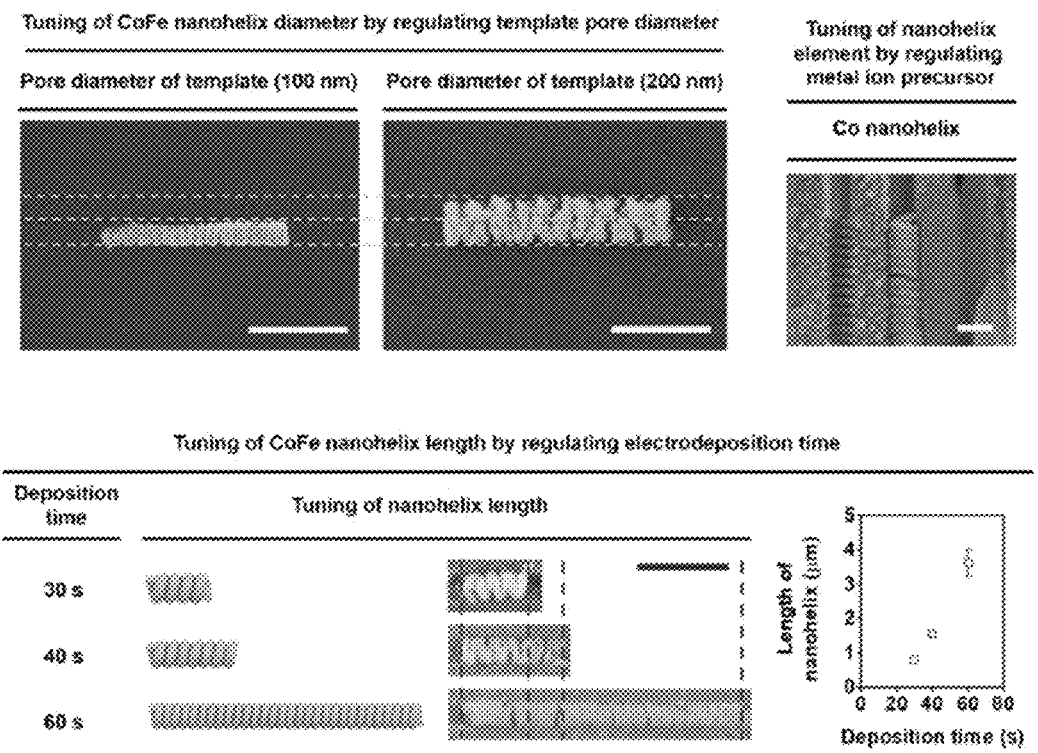

[FIG. 3]
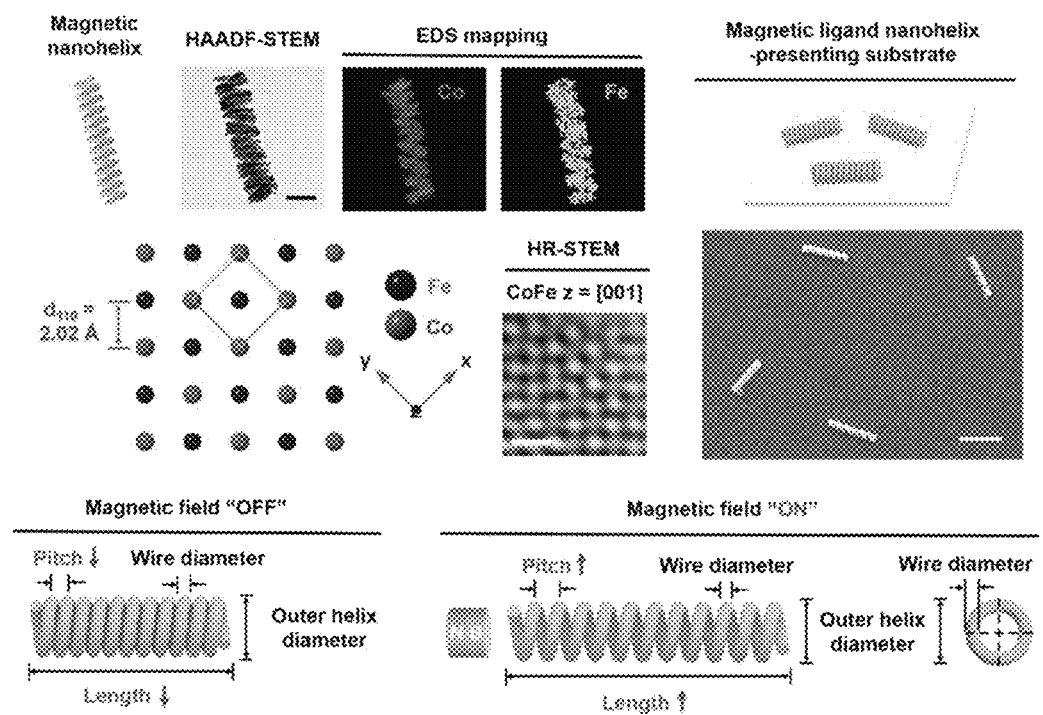

[FIG. 4A]
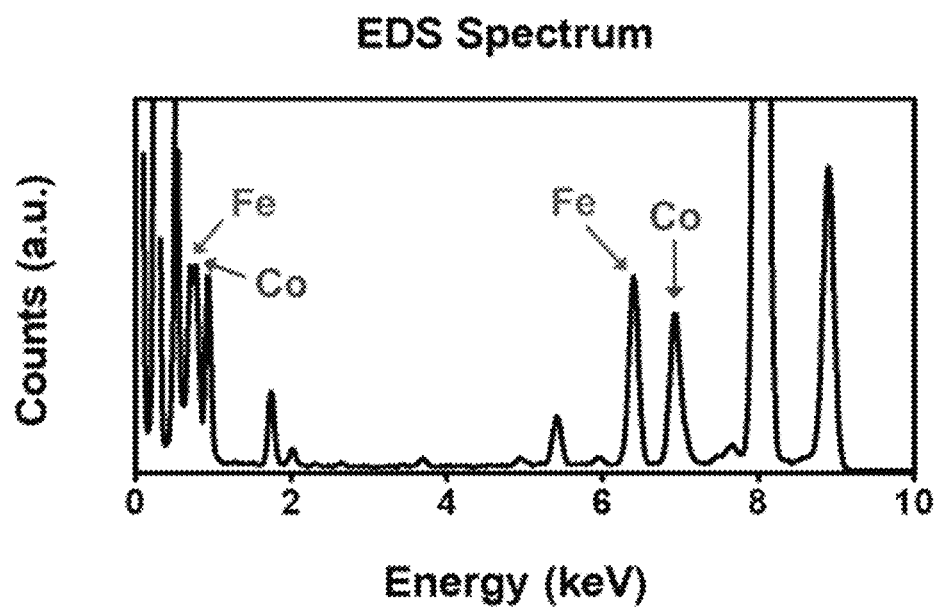

[FIG. 4B]
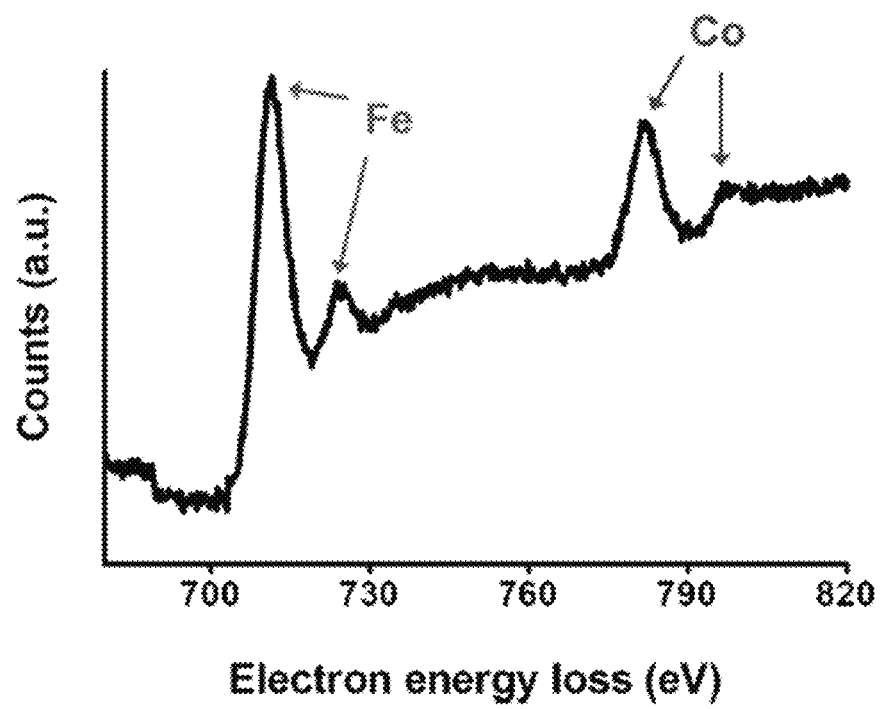

[FIG. 5]
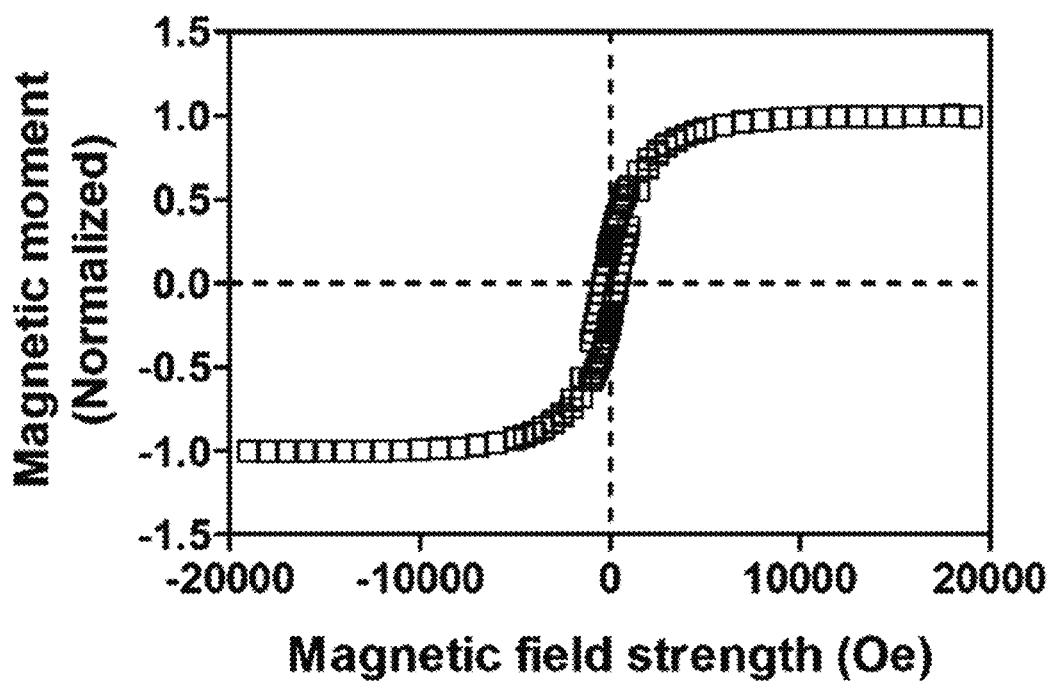

[FIG. 6]
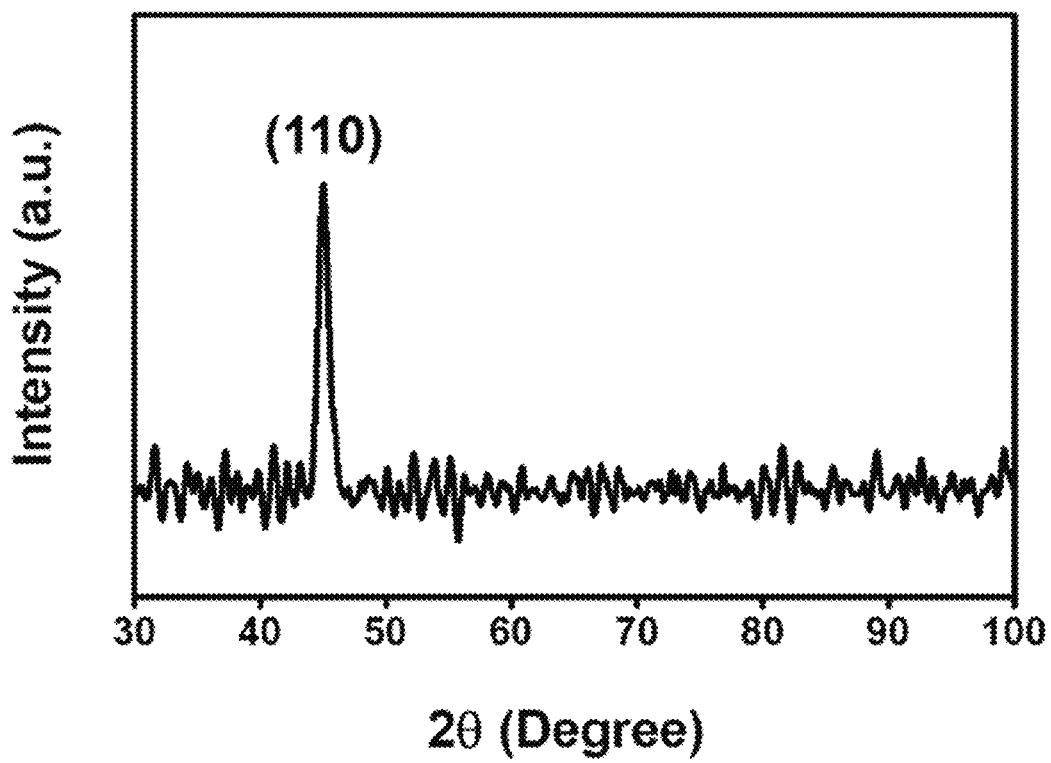

[FIG. 7]
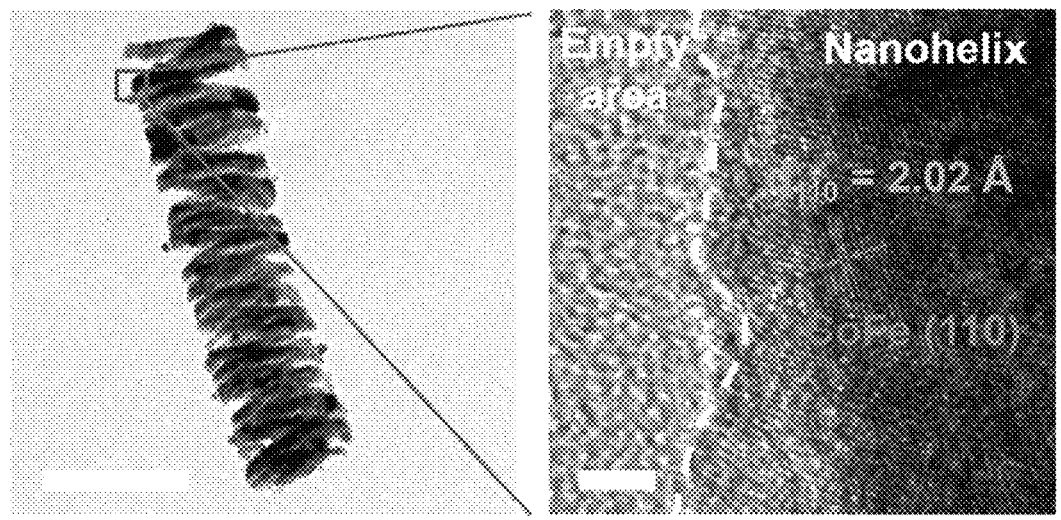

[FIG. 8]
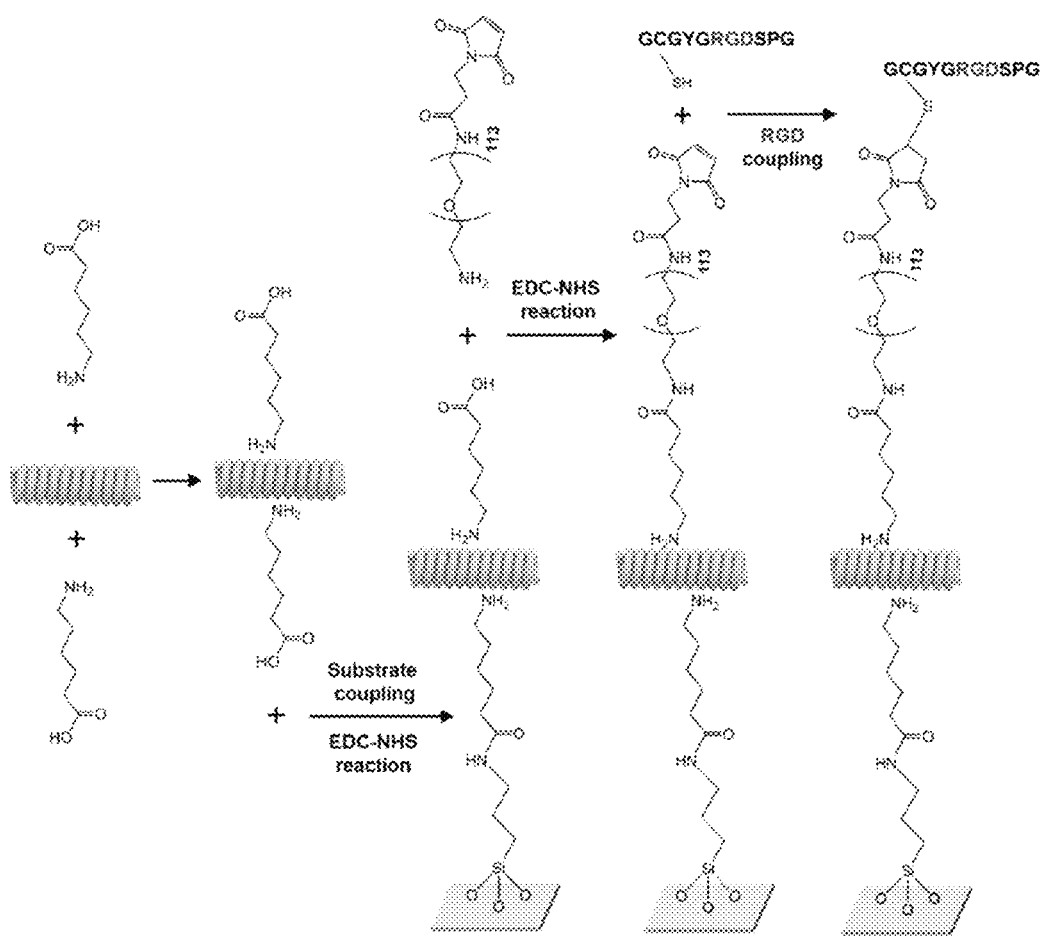

[FIG. 9]
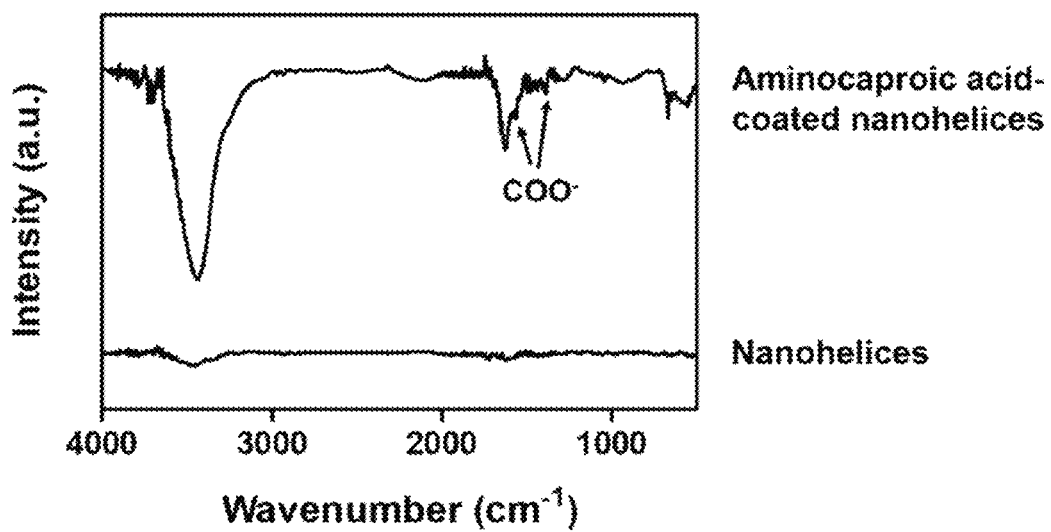

[FIG. 10]
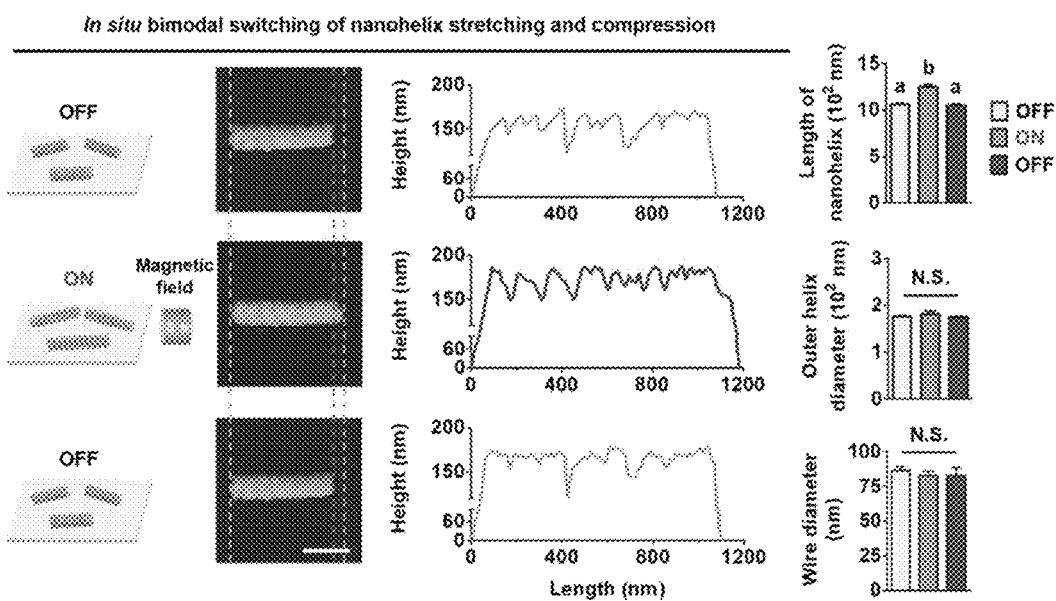

[FIG. 11]
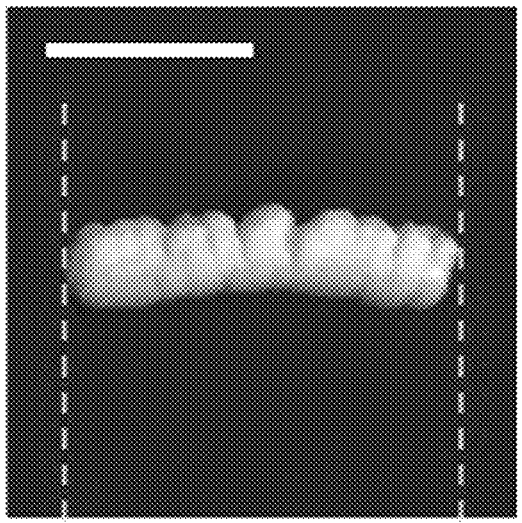
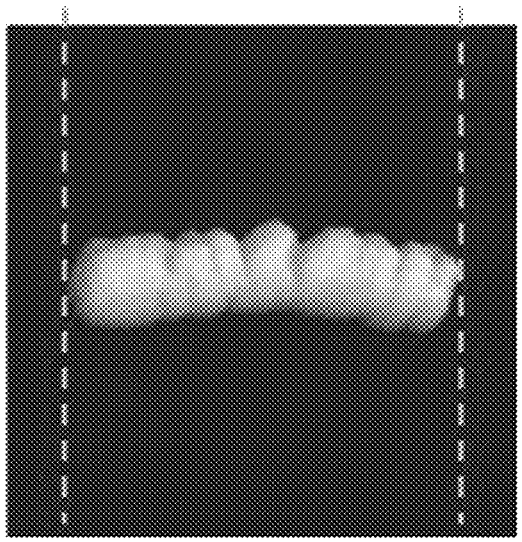

[FIG. 12]
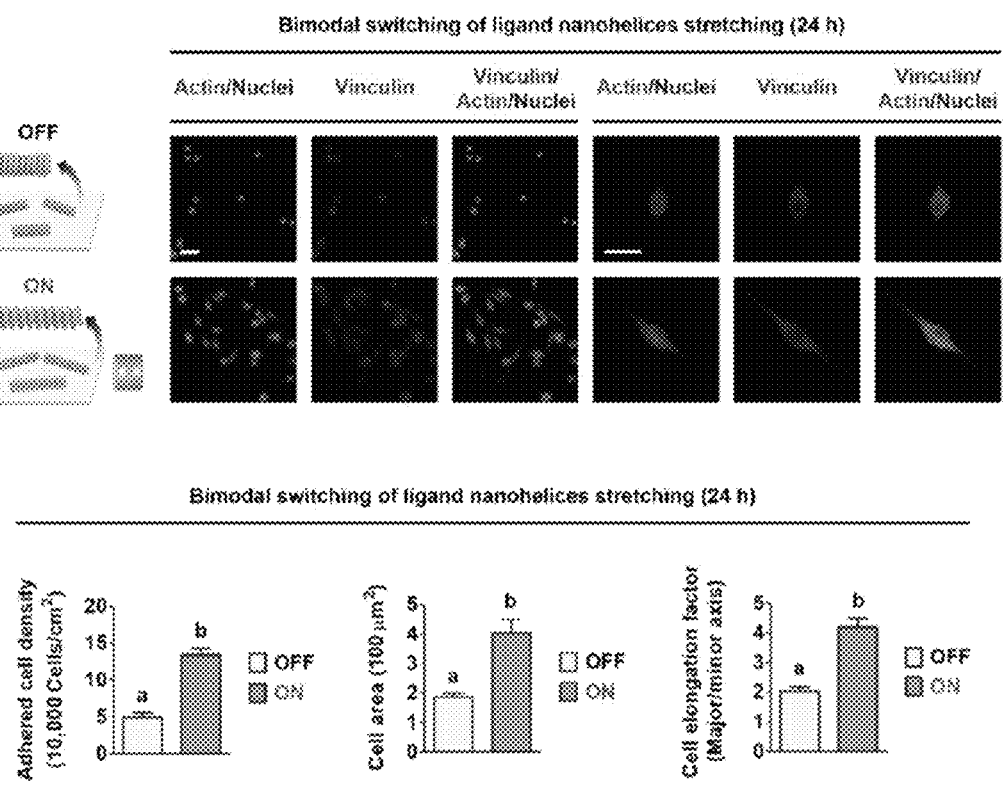

[FIG. 13]
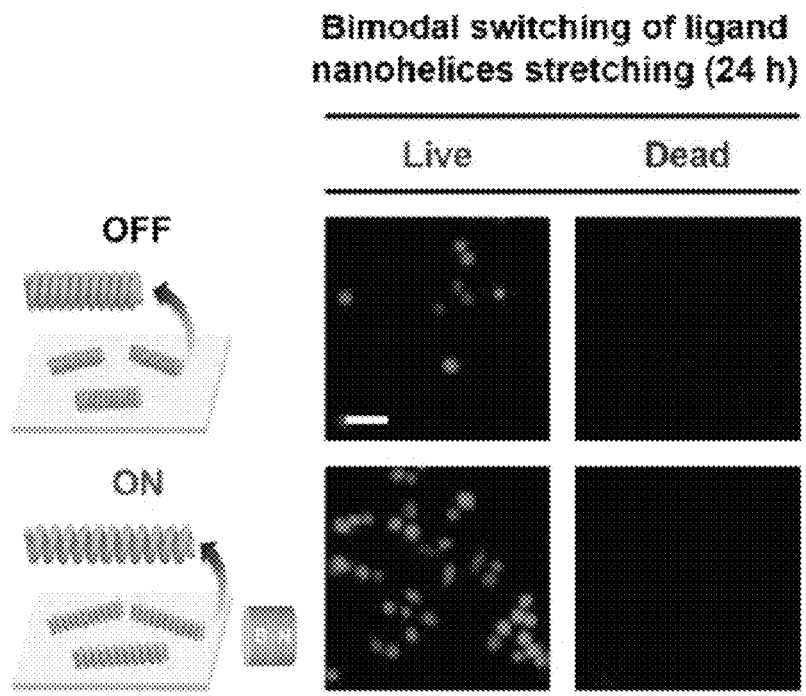
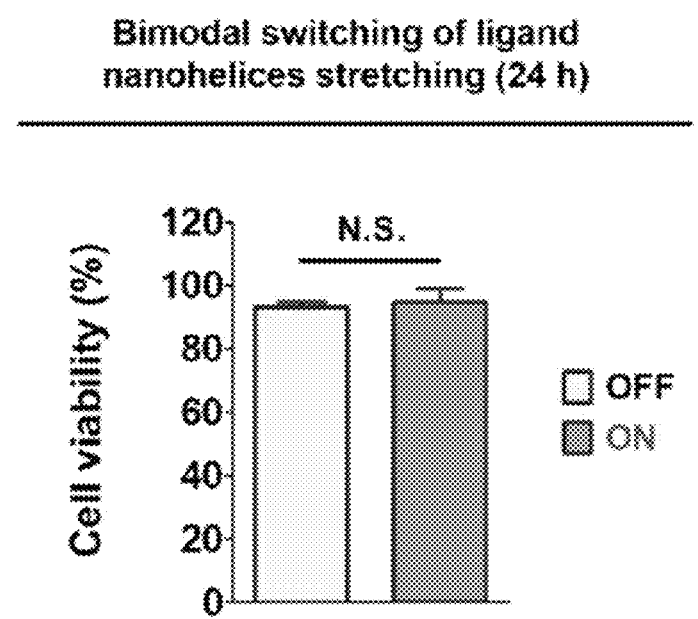

[FIG. 14]
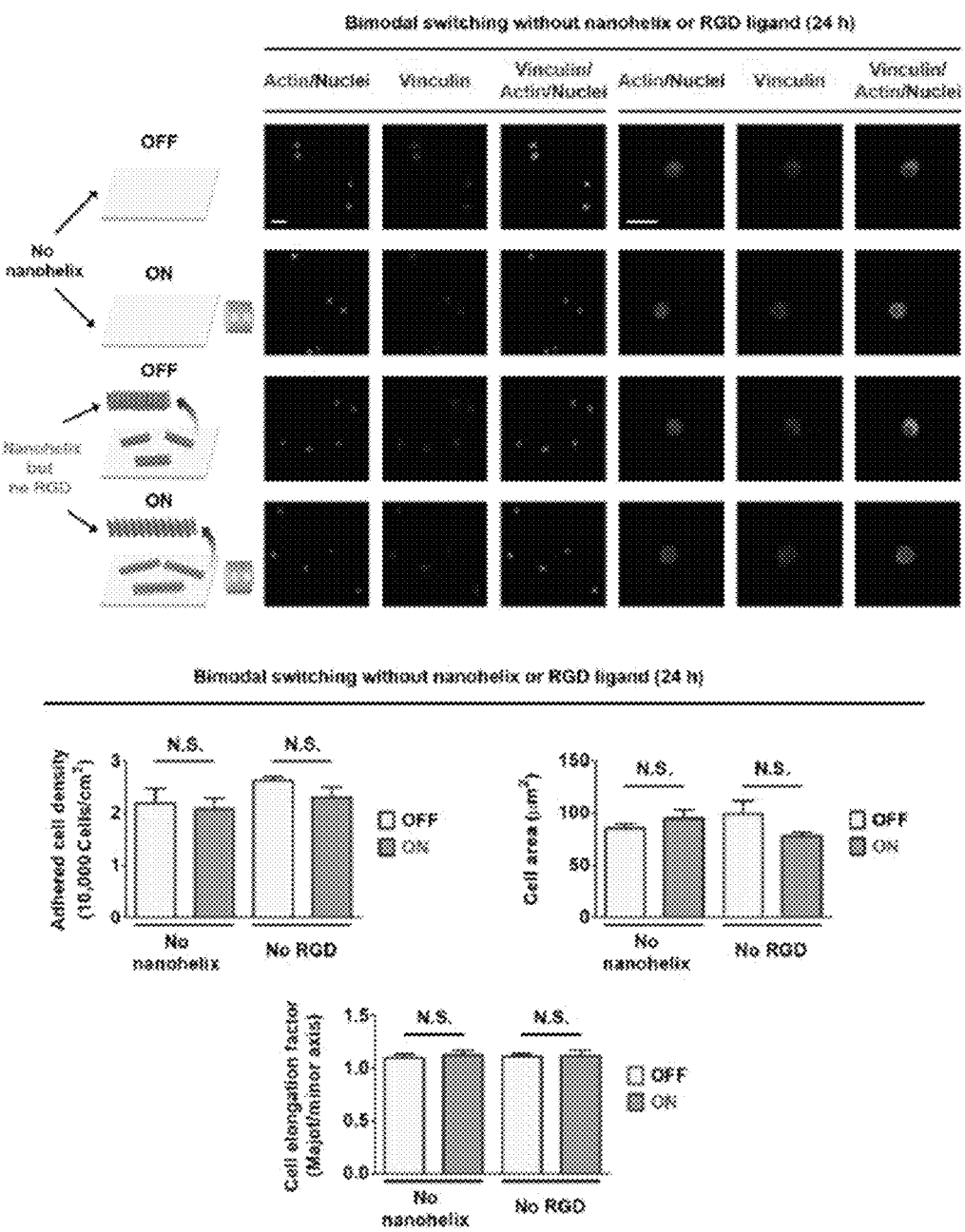

[FIG. 15]
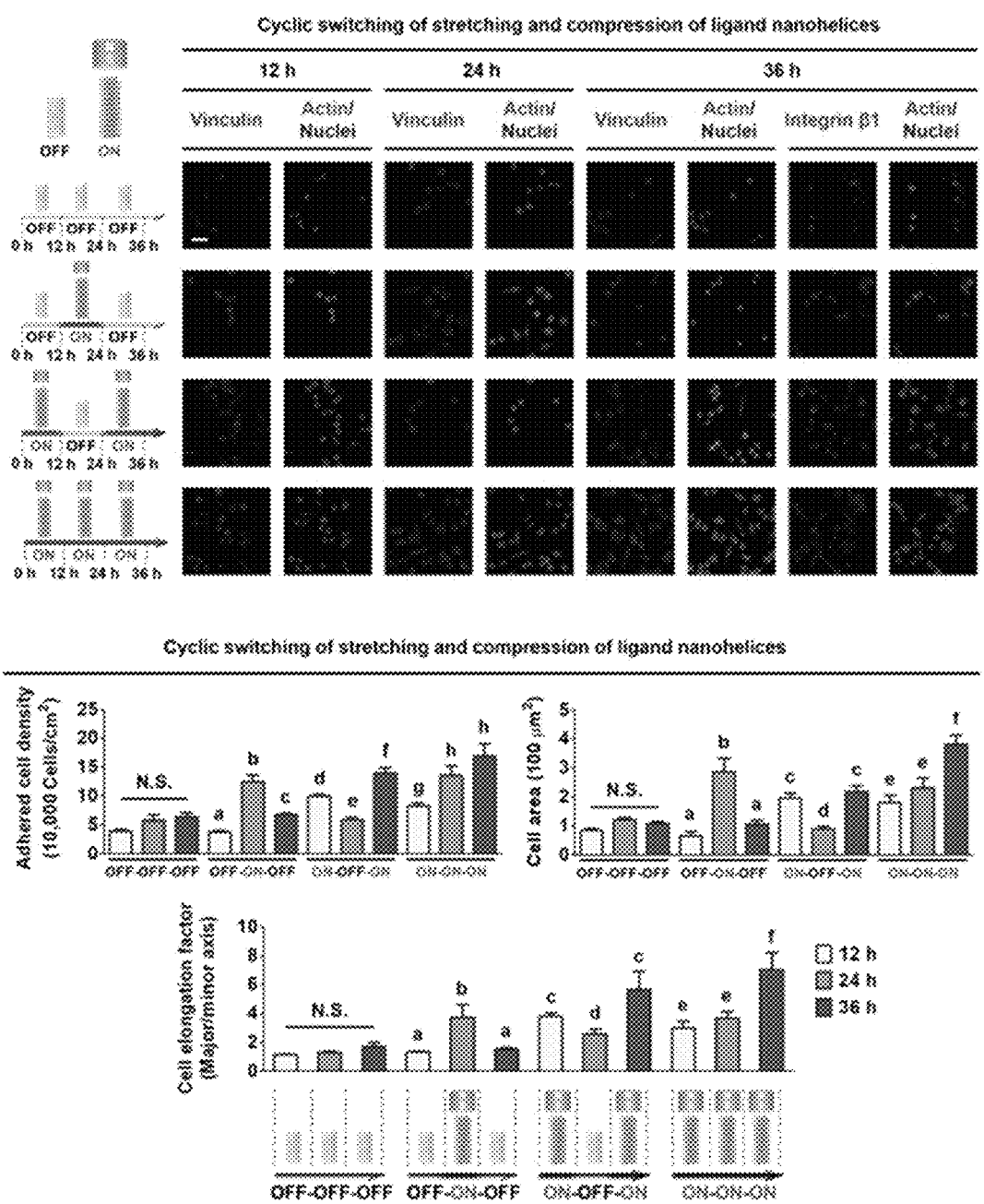

[FIG. 16]
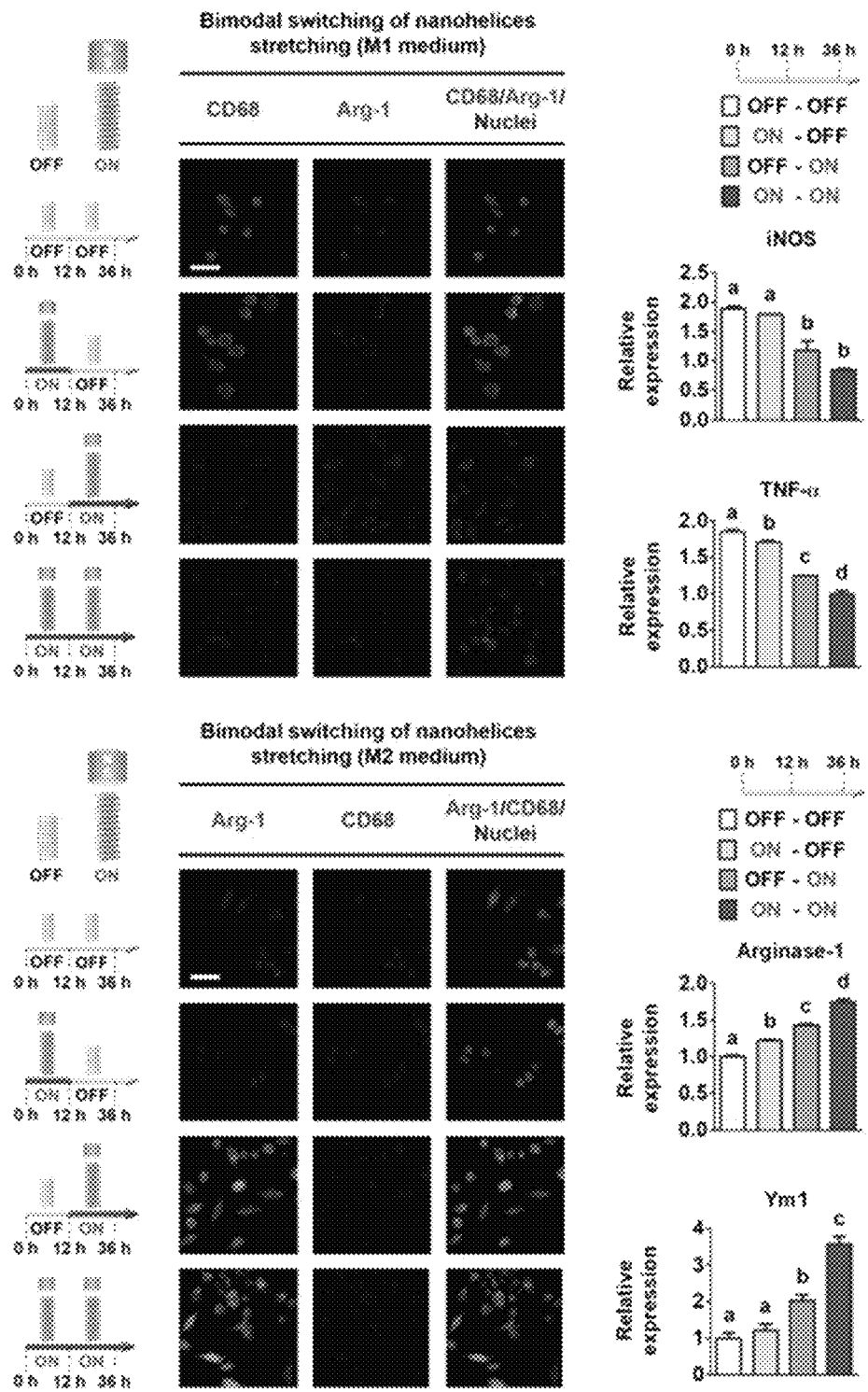

[FIG. 17]
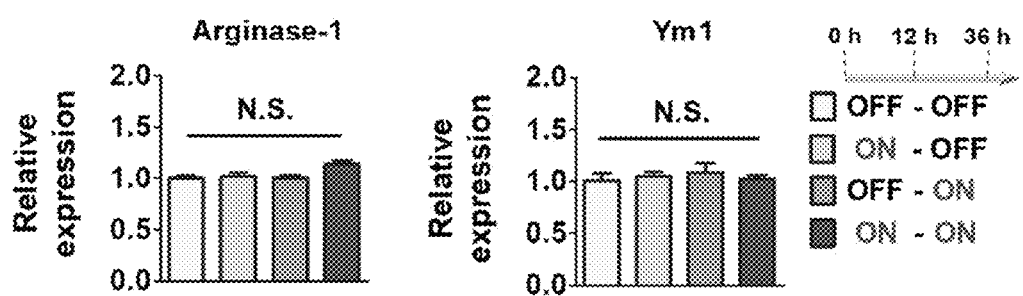
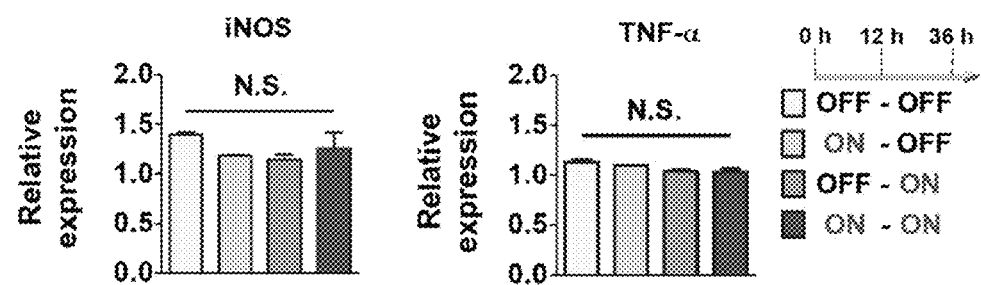

[FIG. 18]
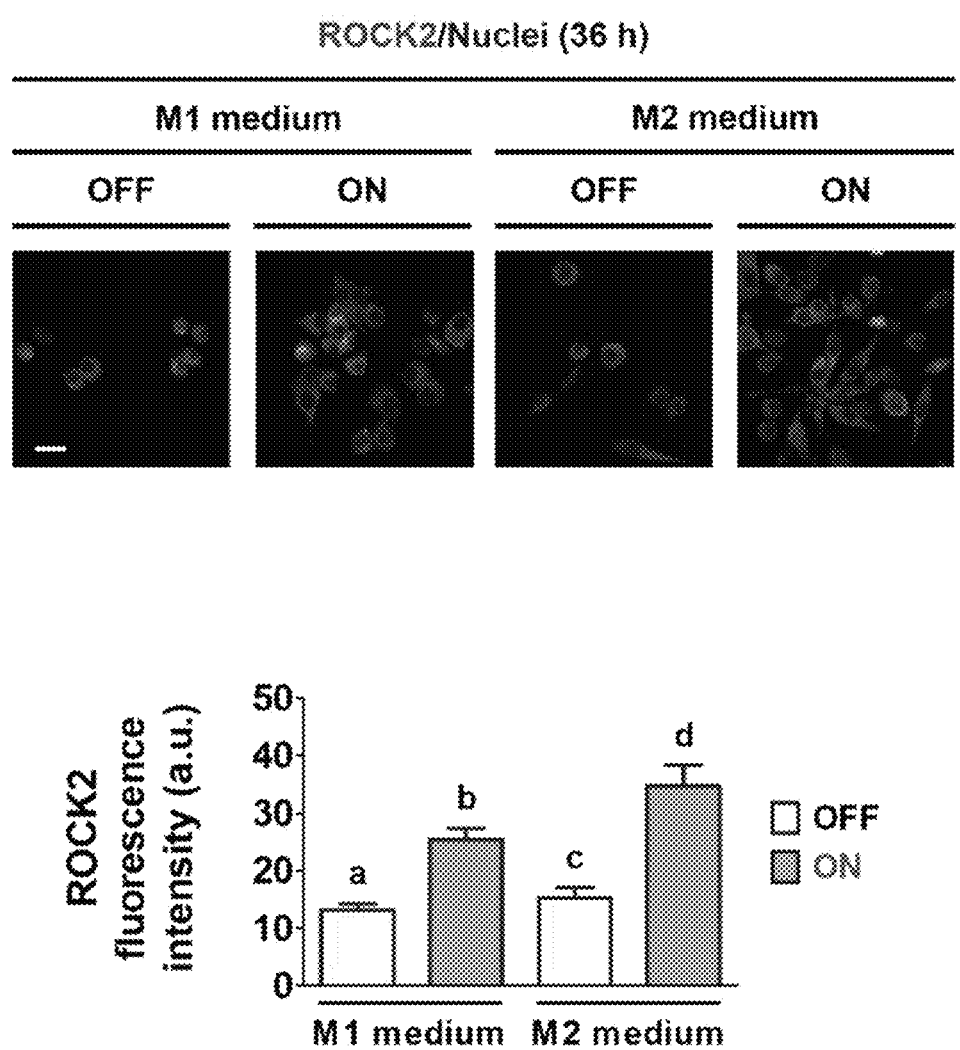

[FIG. 19]
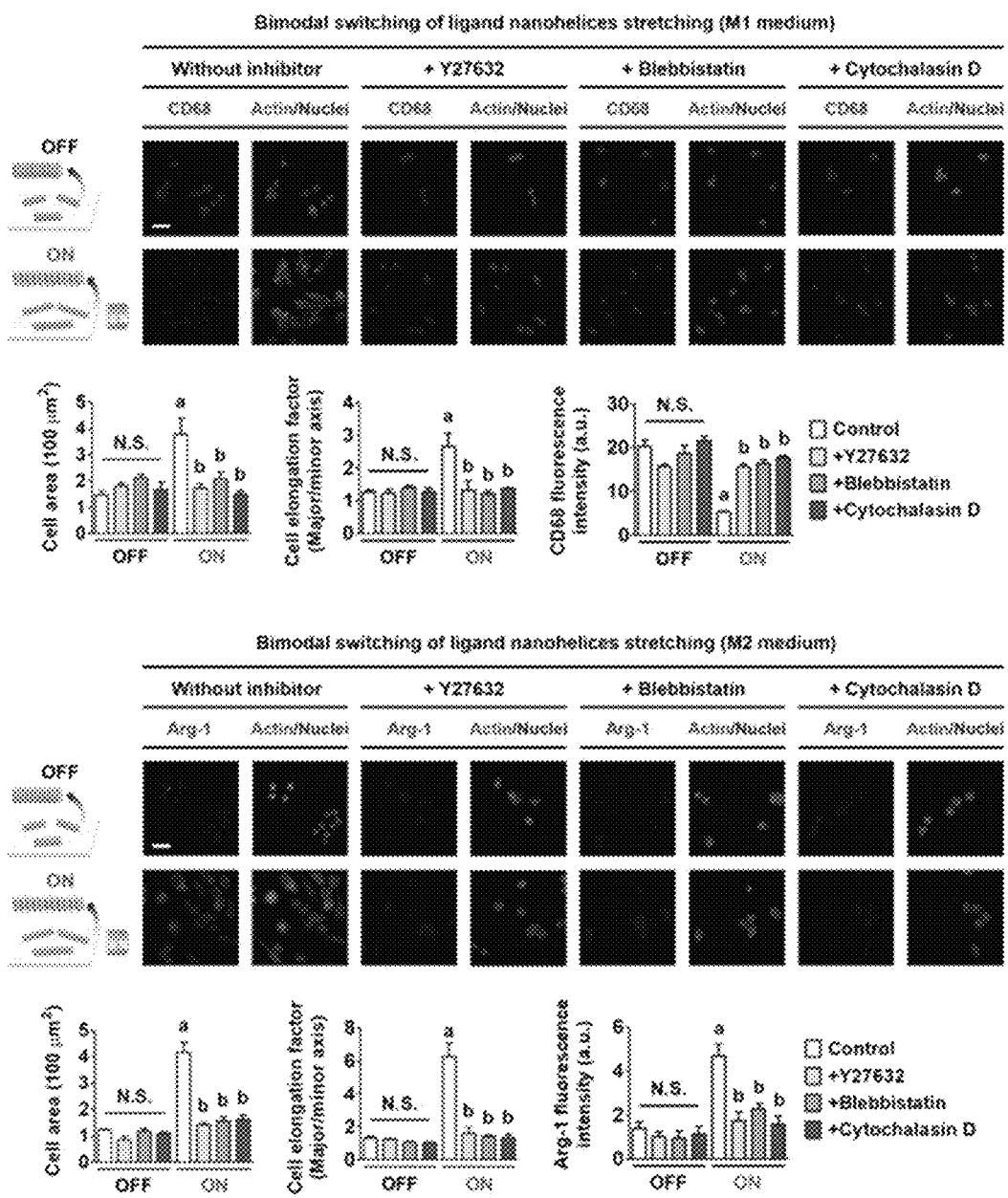

[FIG. 20]
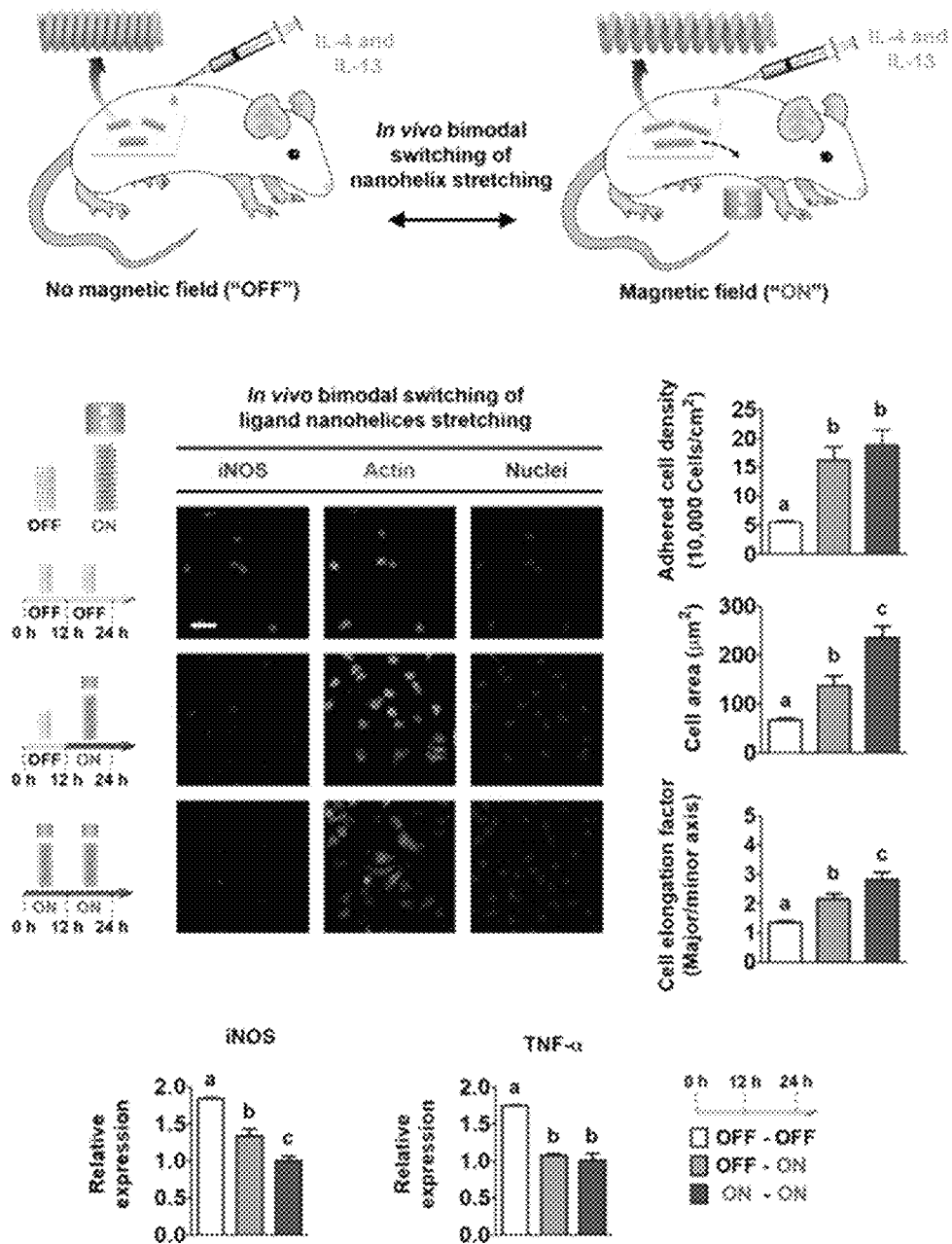

[FIG. 21]
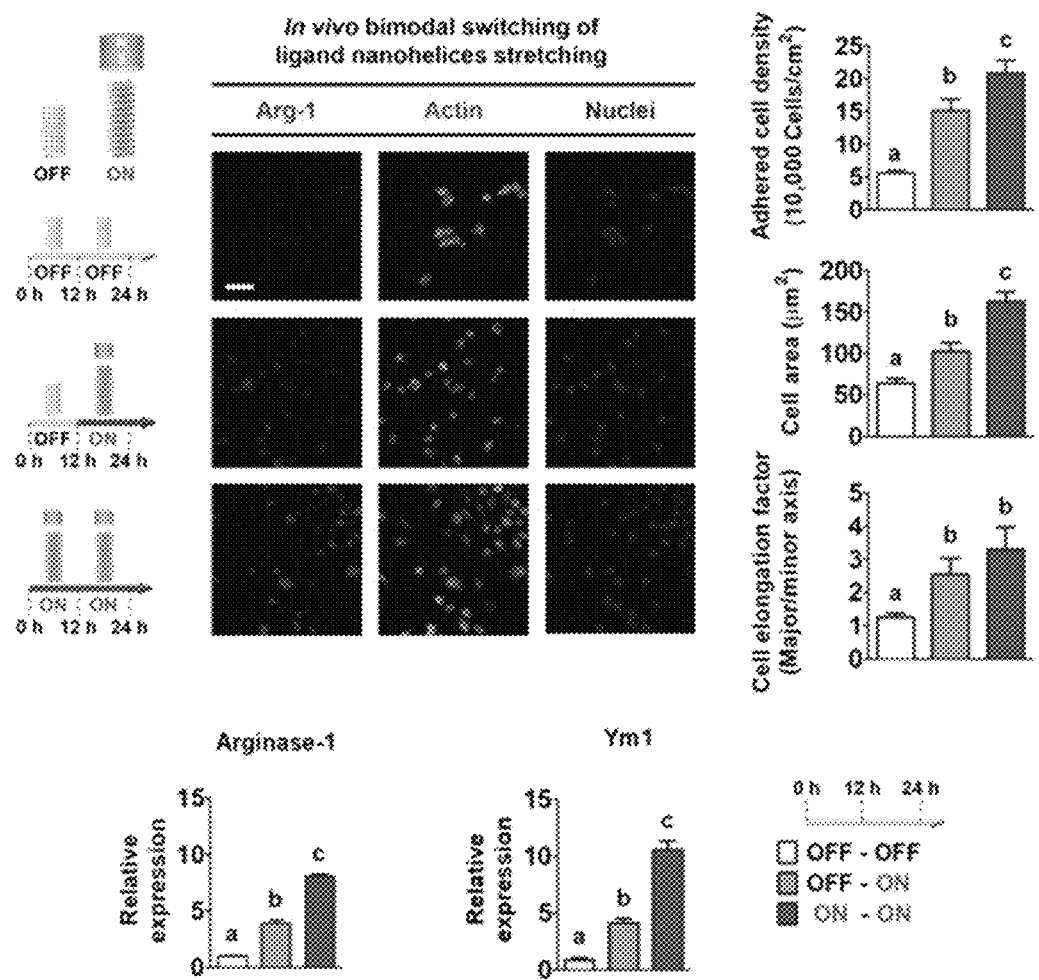

[FIG. 22]
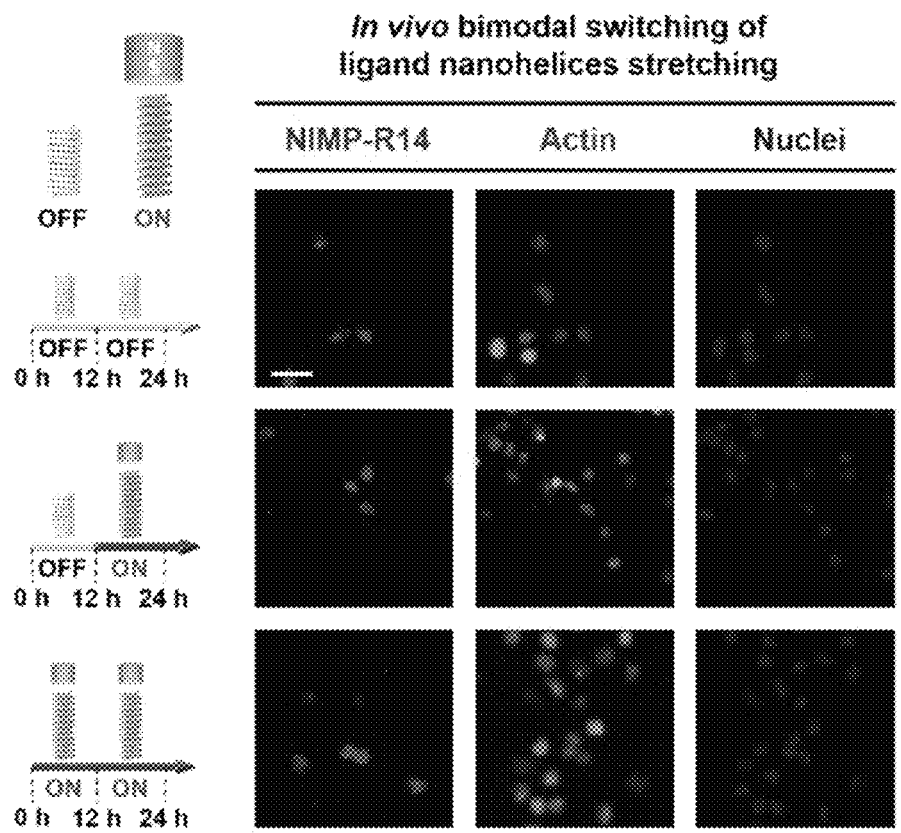
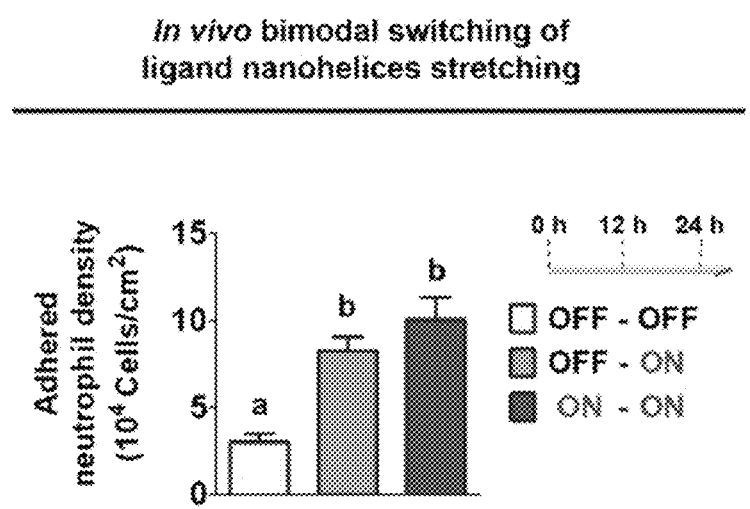

NANOHELIX-SUBSTRATE COMPLEX FOR CONTROLLING MACROPHAGE BEHAVIOR, PREPARATION METHOD THEREOF, AND METHOD OF CONTROLLING ADHESION AND POLARIZATION OF MACROPHAGE BY USING THE SAME

CROSS-REFERENCE TO RELATED APPLICATION

This application claims a benefit under 35 U.S.C. § 119(a) of Korean Patent Application No. 10-2020-0131888 filed on Oct. 13, 2020, on the Korean Intellectual Property Office, the entire disclosure of which is incorporated herein by reference for all purposes.

TECHNICAL FIELD

The present invention relates to a nanohelix-substrate complex for controlling adhesion and polarization of macrophages, a preparation method thereof, and a method of controlling adhesion and polarization of macrophages by using the nanohelix-substrate complex, and particularly, to a method of controlling cell adhesion and polarization of macrophages depending on application/non-application of a magnetic field to the nanohelix-substrate complex.

BACKGROUND ART

A macrophage is the main cell responsible for innate immunity. Most of the macrophages are fixed in the whole body, but some of the macrophages are present in the form of monocytes in the blood. The monocytes may be divided into dendritic cells or macrophages. Most of the macrophages are fixed, representatively include dust cells, microglial cells, Kupffer cells, and Langerhans cells, and the like, and the macrophages are distributed throughout the body, and when antigens invade, the macrophages eat the antigens or secrete toxins to destroy and remove the antigens, and deliver antigens to lymphocytes and trigger an immune response. When an enemy invades the wound, the monocytes in the blood go out of the blood vessels like neutrophils and are divided into macrophages to remove bacteria. Further, the macrophages are divided into a free form which moves to various places in the body and performs phagocytosis, and a fixed form which is fixed to designated organs and performs phagocytosis. The macrophages in the fixed form include liver Kupffer cells, alveolar macrophages, connective tissue structure (histiocyte), and brain microglia cells, and the like.

As a method of efficiently controlling the regeneration and anti-inflammatory effects of macrophages, a technology by the presentation of ligands in vivo is used. However, there is a problem in that the existing micro-scale integrin ligand peptide (RGD) uncaging controls the adhesion of host macrophages, but does not control the functional phenotypic polarization of macrophages.

Accordingly, the applicant of the present invention had developed the technology for controlling adhesion and polarization of macrophages by controlling periodicity and sequences of nanobarcode ligands and filed the technology for a patent application.

In addition, the applicant of the present application intends to propose a technology that is capable of providing a more improved and bio-friendly technology compared to the previously filed macrophage adhesion and polarization control technology below, and particularly, intends to propose a technology that is capable of changing a characteristic of cells in real time by using external stimuli after injection, rather than a method of designing and inserting ligands in advance.

PRIOR ART LITERATURE

Korean Patent No. 10-1916588

SUMMARY OF THE INVENTION

The present invention is conceived to provide a substrate including ligand-coated nanohelices, and a method of controlling adhesion and polarization of macrophages by controlling an application of a magnetic field to the ligand-coated nanohelices.

The present invention provides a nanohelix-substrate complex for controlling adhesion and polarization of macrophages, the nanohelix-substrate complex including: a substrate; one or more nanohelices chemically coupled to the substrate; and one or more integrin ligand peptides chemically coupled to the nanohelix, in which the nanohelix is formed of a nanowire in the spiral form and includes one or more metal elements, the nanohelix has a length of 100 nm to 20 μm, and the nanohelix has a length reversibly changed depending on application/non-application of a magnetic field within a range of Equation 1 below.

$$|L_1-L_0|>10 \text{ nm} \quad \text{[Equation 1]}$$

In Equation 1, $L_1$ is a length of the nanohelix when the magnetic field is applied, and $L_0$ is a length of the nanohelix when the magnetic field is not applied.

Further, the present invention provides a method of preparing a nanohelix-substrate complex for controlling adhesion and polarization of macrophages, the method including: preparing a nanohelix by electrodepositing a solution including two or more metal elements; coupling a carboxylate substituent to the nanohelix by mixing the nanohelix and a first suspension; manufacturing a substrate coupled with the nanohelix by soaking a substrate of which a surface is activated in a solution containing the nanohelix to which the carboxylate is coupled; coupling a linker to a distal end of the nanohelix by soaking the substrate coupled with the nanohelix in a solution containing a polyethylene glycol linker; and coupling an integrin ligand peptide (RGD) to the nanohelix by mixing a second suspension containing the integrin ligand peptide (RGD) and the activated substrate coupled with the nanohelix.

Furthermore, the present invention provides a method of controlling adhesion and polarization of macrophages, the method including: controlling cell adhesion and polarization of macrophages by treating the nanohelix-substrate complex for controlling cell adhesion and polarization of the macrophages according to claim 1 with a culture medium and then applying a magnetic field in a range from 20 mT to 7 T, in which the nanohelix has a length reversibly changed within Equation 1 below depending on application/non-application of the magnetic field.

$$|L_1-L_0|>10 \text{ nm} \quad \text{[Equation 1]}$$

In Equation 1, $L_1$ is a length of the nanohelix when the magnetic field is applied, and $L_0$ is a length of the nanohelix when the magnetic field is not applied.

The nanohelix-substrate complex for controlling adhesion and polarization of macrophages according to the present invention may reversibly control adhesion and polarization of macrophages by controlling application/non-application of a magnetic field to the nanohelix coated with the integrin ligand peptide, thereby efficiently controlling adhesion and phenotypic polarization of macrophages in vivo and ex vivo.

BRIEF DESCRIPTION OF THE DRAWINGS

The patent or application file contains a least one drawing executed in color. Copies of this patent or patent application publication with color drawing(s) will be provided by the Office upon request and payment of the necessary fee.

FIG. 1 is a schematic diagram illustrating a nanohelix-substrate complex for controlling cell adhesion and polarization of macrophages and a method of controlling adhesion and polarization of macrophages by using the same according to an exemplary embodiment of the present invention.

FIG. 2 is a scanning electron microscope image of a nanohelix according to the present invention.

FIG. 3 is a High-Angle Annular Dark Field Scanning Transmission Electron Microscope (HAADF-STEM) image, a Scanning Electron Microscope (SEM) image, an Energy Dispersive Spectroscopy (EDS) mapping image, and a High-Resolution Scanning Transmission Electron Microscopy (HR-STEM) image of the nanohelix according to the present invention, and a scale bar of the HAADF-STEM and the EDS represent 250 nm, a scale bar of the SEM represents 1 μm, and a scale bar of the HR-STEM represents 4 Å.

FIG. 4A is a graph illustrating an EDS analysis result and FIG. 4B is a graph illustrating an EELS analysis result of the nanohelix according to the present invention.

FIG. 5 is a graph illustrating a vibrating-sample magnetometry measurement result of the nanohelix according to the present invention.

FIG. 6 is an X-ray diffraction analysis graph of the nanohelix according to the present invention.

FIG. 7 is a High-Resolution Transmission Electron Microscopy (HRTEM) image of the nanohelix according to the present invention, the left scale bar represents 300 nm, and the right scale bar represents 2 nm.

FIG. 8 is an image schematically illustrating an operation of preparing a nanohelix-substrate complex according to the present invention.

FIG. 9 is a diagram illustrating a result of a Fourier Transform Infrared Spectroscopy (FT-IR) analysis of the nanohelix-substrate complex according to the present invention.

FIGS. 10 and 11 are Atomic Force Microscope (AFM) images of the nanohelix according to the present invention, and a scale bar represents 500 nm.

FIG. 12 is a confocal immunofluorescent image of F-actin, nuclei, and vinculin in macrophages cultured (after 24 hours) by using the nanohelix-substrate complex according to the present invention, and a graph illustrating a cell density, a cell area, and a cell elongation factor calculated based on the result of the confocal immunofluorescent experiment, and a scale bar represents 20 μm.

FIG. 13 is a confocal immunofluorescent image of live cells and dead cells in macrophages cultured (after 24 hours) by using the nanohelix-substrate complex according to the present invention, and a graph illustrating cell viability calculated based on the result of the confocal immunofluorescent experiment, and a scale bar represents 50 μm.

FIG. 14 is a diagram illustrating a result of an adhesion experiment of macrophages for bimodal switching in a substrate with no nanohelix or the nanohelix-substrate complex in which integrin ligand (RGD) is not coupled according to a comparative example of the present invention.

FIG. 15 is a confocal immunofluorescent image of F-actin, nuclei, and vinculin in macrophages cultured for 36 hours by regulating application of a magnetic field at an interval of 12 hours by using the nanohelix-substrate complex according to the present invention, and a scale bar represents 20 μm.

FIG. 16 is a result of an experiment of the control of macrophage adhesion-dependent phenotypic polarization by application of a magnetic field by using the nanohelix-substrate complex according to the present invention, and a scale bar represents 20 μm.

FIG. 17 is a result of an experiment for controlling application of a magnetic field when there is no stimulation medium matched to a polarization phenotype (that is, M1 expression in an M2-stimulation medium or M2 expression in an M1-stimulation medium) by using the nanohelix-substrate complex according to the present invention.

FIG. 18 is a confocal immunofluorescent image of ROCK2 and nuclei after macrophages are cultured in an M1 or M2 medium under bimodal switching of stretching ("ON") in which a magnetic field is applied and compression ("OFF") in which a magnetic field is not applied for 36 hours, and a graph illustrating ROCK2 immunofluorescent intensity calculated based on a result of the confocal immunofluorescent experiment, and a scale bar represents 20 μm.

FIG. 19 is a diagram illustrating an experiment using the nanohelix-substrate complex according to the exemplary embodiment of the present invention, and a confocal immunofluorescent image of Arg-1, and F-actin, and nuclei in macrophages cultured in an M1 polarization medium with and without an inhibitor for ROCK(Y27632), myosin II (blebbistatin), or actin polymerization (cytochalasin D) for 36 hours and a graph representing a cell area, a cell elongation factor, and CD68 fluorescence intensity calculated based on the confocal immunofluorescent experiment result, and a confocal immunofluorescent image of Arg-1, and F-actin, and nuclei in macrophages cultured in an M2 polarization medium with and without an inhibitor for ROCK(Y27632), myosin II (blebbistatin), or actin polymerization (cytochalasin D) and a graph representing a cell area, a cell elongation factor, and Arg-1 fluorescence intensity calculated based on the confocal immunofluorescent experiment result.

FIGS. 20 and 21 are diagrams illustrating a result of an experiment for control of adhesion and phenotype of host macrophages in vivo by using the nanohelix-substrate complex according to the present invention.

FIG. 22 is a diagram illustrating a result of an experiment of adhesion in vivo of host neutrophil to the substrate by using the nanohelix-substrate complex according to the present invention.

DETAILED DESCRIPTION

Hereinafter, in order to describe the present invention in more specifically, an exemplary embodiment of the present invention will be described in more detail with reference to the accompanying drawings. However, the present invention is not limited to the exemplary embodiment described herein, and may also be specified in other forms.

The present invention provides a nanohelix-substrate complex for controlling adhesion and polarization of macrophages, the nanohelix-substrate complex including: a substrate; one or more nanohelices chemically coupled to the substrate; and one or more integrin ligand peptides chemically coupled to the nanohelix, in which the nanohelix is provided with a nanowire in a spiral form, includes one or more metal elements, has a length of 100 nm to 20 μm, and has a length reversibly changed depending on application/non-application of a magnetic field within a range of Equation 1 below.

$$|L_1-L_0|>10 \text{ nm} \quad \text{[Equation 1]}$$

In Equation 1, $L_1$ is a length of the nanohelix when a magnetic field is applied, and $L_0$ is a length of the nanohelix when a magnetic field is not applied.

FIG. 1 is a schematic diagram illustrating a nanohelix-substrate complex for controlling cell adhesion and polarization of macrophages and a method of controlling cell adhesion and polarization of macrophages by using the same according to an exemplary embodiment of the present invention.

Referring to FIG. 1, the nanohelix-substrate complex of the present invention includes: a substrate; one or more nanohelices chemically coupled to the substrate; and one or more integrin ligand peptides chemically coupled to the nanohelix, in which the nanohelix is provided with a nanowire in a spiral form and the nanowire includes one or more metal elements among cobalt (Co), iron (Fe), and nickel (Ni).

In particular, the nanohelix may be provided with a nanowire in a spiral form satisfying Equation 1.

$$|L_1-L_0|>10 \text{ nm} \quad \text{[Equation 1]}$$

In Equation 1, $L_1$ is a length of the nanohelix when a magnetic field is applied, and $L_0$ is a length of the nanohelix when a magnetic field is not applied.

In Equation 1, the length of the nanohelix when the magnetic field is not applied may be 100 nm to 20 μm, 500 nm to 4 μm, or 1 μm to 3 μm.

As described above, when the magnetic field is applied, the nanohelix is stretched and has an increasing length, thereby promoting adhesion and M2 polarization of macrophages in vivo. However, when the magnetic field is removed, the nanohelix is compressed, so that the length of the nanohelix returns to the existing length.

In particular, in Equation 1, the change in the length of the nanohelix depending on application/non-application of the magnetic field may be 10 nm or more, 20 nm or more, 10 nm to 500 nm, or 10 nm to 100 nm.

When the change in the length of the nanohelix in the nanohelix-substrate complex of the present invention does not satisfy Equation 1, the change in the length of the nanohelix is small, so there is no difference in cell adhesion, which is a problem.

An average length of a spiral outer diameter of the nanohelix may be 50 nm to 200 nm, or 100 nm to 200 nm. When the spiral outer diameter of the nanohelix is less than 100 nm, the nanohelix is too small, so that it is difficult for the integrin ligand peptide to be coupled at regular intervals, and when the spiral outer diameter of the nanohelix is larger than 200 nm, an area occupied by the nanohelix on the substrate is large, so that there is a problem in that it is difficult to distribute the nanohelices on the substrate at an appropriate density.

The nanohelix is formed of a nanowire, and the nanowire may include one or two or more metal elements among cobalt (Co), iron (Fe), and nickel (Ni), and the nanowire may be provided in the form of a wire having a circular cross-section, and has a diameter of 5 nm to 100 nm, 20 nm to 90 nm, or 60 nm to 90 nm. When the foregoing diameter of the wire is not satisfied, the nanohelices may not exhibit smooth stretching and compression.

The integrin ligand peptide coupled into the nanohelix may be a thiolated integrin ligand peptide, and the plurality of integrin ligand peptides is coupled to the nanohelix while being spaced apart from each other, and an average interval between the adjacent integrin ligand peptides may be 1 nm to 10 nm. When the average interval between the adjacent integrin ligand peptides is less than 1 nm, it is difficult to activate adhesion and polarization of macrophage even in the case where a magnetic field is applied, and when the average interval between the adjacent integrin ligand peptides is larger than 10 nm, adhesion and polarization of macrophage are activated even in the case where a magnetic field is not applied, so that there is a problem in that it is difficult to reversibly control the adhesion and polarization of macrophage by using the magnetic field.

When the magnetic field is applied to the nanohelix, the adjacent spirals in the nanohelix are spaced apart from each other, and a pitch between the adjacent spirals may be 1 nm to 100 nm, 1 nm to 50 nm, or 5 nm to 30 nm. In this case, when the magnetic field is applied, the pitch interval increases while the nanohelix is stretched. Accordingly, an interval between the integrin ligand peptides may also increase.

The integrin ligand peptide is the thiolated integrin ligand peptide, and a thiol group of the integrin ligand peptide may be coupled to the spiral nanohelices by a polyethylene glycol linker. The polyethylene glycol linker may be maleimide-poly(ethylene glycol)-NHS ester (Mal-PEG-NHS ester). The nanohelix includes the polyethylene glycol linker, so that coupling force between the nanohelix and the integrin ligand peptide increases to improve durability.

The nanohelix may have a structure in which carboxylate is coupled. The carboxylate substituent may be an amino acid derivate, in particular, aminocaproic acid. As described above, the nanohelix has the structure in which carboxylate is coupled, thereby increasing coupling force between the nanohelix and the substrate and the integrin ligand peptide.

The substrate is the substrate of which a surface is aminated, and may be the substrate, of which the surface is activated, by soaking the substrate in an aminosilane solution, and may have a structure in which the amino group on the surface of the substrate is coupled to a carboxyl group of the nanohelix through the EDC/NHS reaction.

Further, the substrate may be the substrate which is not coupled with the nanohelix and of which the surface is inactivated.

Further, the present invention provides a method of preparing a nanohelix-substrate complex for controlling adhesion and polarization of macrophages, the method including: preparing a nanohelix by electrodepositing a solution containing one or more metal elements; coupling a carboxylate substituent to the nanohelix by mixing the nanohelix and a first suspension; manufacturing a substrate coupled with the nanohelix by soaking a substrate of which a surface is activated in a solution containing the nanohelix to which the carboxylate is coupled; coupling a linker to a distal end of the nanohelix by soaking the nanohelix-coupled substrate in a solution containing a polyethylene glycol linker; and coupling an integrin ligand peptide (RGD) to the nanohelix by mixing a second suspension containing the integrin ligand peptide (RGD) and the activated substrate coupled with the nanohelix.

In the preparing of the nanohelix, the solution containing the metal element may include one or two or more metal elements among cobalt (Co), iron (Fe), and nickel (Ni).

The preparing of the nanohelix includes: preparing a nano template including nano pores, and including a working electrode on one surface thereof; preparing a first metal precursor mixed solution containing a metal precursor solution containing ascorbic acid ($C_6H_8O_6$), vanadium (IV) oxide sulfate ($VOSO_4.xH_2O$), and a metal to be deposited; preparing a second metal precursor mixed solution by mixing the first metal precursor mixed solution and nitric acid ($HNO_3$); immersing the nano template in the second metal precursor mixed solution, and depositing metal nanohelices on the nano pores by an electrodepositing method by applying a current between a counter electrode and the working electrode inserted into the second metal precursor mixed solution; and selectively removing the working electrode and the nano template in the nano template on which the metal nanohelices are deposited.

As the nano template, an Anodic Aluminum Oxide (AAO) nanoframe, an inorganic nanoframe, or a polymer nanoframe is used. Herein, the case of using the AAO nanoframe is illustrated. A size of the nanowire is determined according to a diameter of a pore of the AAO nanoframe, and a length of the nanowire is determined according to a forming time and speed of the nanowire.

An average diameter of the nano pore may be 5 to 500 nm, 50 nm to 200 nm, or 100 nm to 200 nm.

The metal precursor solution may include at least one of cobalt sulfate (II) heptahydrate ($CoSO_4.7H_2O$) and iron sulfate (II) heptahydrate ($FeSO_4.7H_2O$).

A concentration of cobalt sulfate (II) heptahydrate ($CoSO_4.7H_2O$) may be 30 mM to 100 mM, a concentration of vanadium(IV) oxide sulfate ($VOSO_4.xH_2O$) may be 30 mM to 100 mM, a concentration of iron sulfate(II) heptahydrate ($FeSO_4.7H_2O$) may be 30 mM to 100 mM, and a concentration of ascorbic acid ($C_6H_8O_6$) may be 20 mM to 50 mM.

pH of the second mixed precursor mixed solution may be 1.5 to 2.5.

The method may further include immersing the nano template in the second metal precursor mixed solution and decompressing a plating bath containing the second metal precursor mixed solution. Pressure of the plating bath may be 100 Torr to 700 Torr.

A density of a current flowing in the working electrode during the electroplating may be 0.1 to 300 $mA/cm^2$, and an electroplating time may be one minute to 48 hours.

A silver (Ag) electrode layer having a thickness of 250 nm is formed on a bottom surface of the AAO nanoframe by an electron beam evaporation method. The electrode layer serves as a negative electrode during the electrodeposition. Herein, as the electrode layer, other metals or other conductive material layers may be used.

The coupling of the carboxylate substituent may be performed by mixing the nanohelix and the first suspension and reacting the nanohelix and the first suspension for 8 to 20 hours to 10 to 15 hours. The first suspension may contain an amino acid derivative containing a carboxylate substituent, and specifically, the amino acid derivative may be aminocaproic acid. The amino acid derivative may be coupled to the surface of the nanohelix by reacting the nanohelix with the first suspension.

The manufacturing of the substrate coupled with the nanohelix may be performed by soaking the substrate, of which the surface is activated, in the solution containing the nanohelix in which the carboxylate is coupled.

The substrate, of which the surface is activated, may be manufactured by immersing the substrate in the acidic solution containing any one or more of hydrochloric acid and sulfuric acid for 30 minutes to 2 hours or 30 minutes to 1 hour. Through this, the coupling with an amino group is facilitated by coupling a hydroxyl group to the surface of the substrate, thereby effectively performing activation of the surface of the substrate.

In the manufacturing of the substrate coupled with the nanohelix, the surface of the substrate may be aminated by soaking the substrate, of which the surface is activated, in the amino-silane solution under a dark condition. The amino-silane solution may include (3-aminopropyl)triephoxysilane (APTES). In this case, the amination of the surface of the substrate means that the amine group is coupled onto the substrate. The surface of the substrate is aminated by immersing the substrate in the amino-silane solution, so that the substrate may be coupled with the nanohelix through the EDC/NHS reaction.

The coupling of the linker to the distal end of the nanohelix may be performed by soaking the nanohelix-coupled substrate in the solution containing the polyethylene glycol linker. The polyethylene glycol linker may be maleimide-poly(ethylene glycol)-NHS ester (Mal-PEG-NHS ester). The nanohelix includes the polyethylene glycol linker, so that coupling force between the nanohelix and the integrin ligand peptide increases to improve durability.

The coupling of the integrin ligand peptide to the nanohelix may be performed by mixing a second suspension including the integrin ligand peptide (RGD) and the activated nanohelix-coupled substrate. The second suspension may include the thiolated integrin ligand peptide.

The method may further include soaking the nanohelix-coupled substrate in a solution including a polyethylene glycol derivative and inactivating the surface of the substrate that is not coupled with the nanohelix, after the coupling of the integrin ligand peptide to the nanohelix. The polyethylene glycol derivative may be methoxy-poly(ethylene glycol)-succinimidylcarboxymethyl ester.

Further, the present invention provides a method of controlling adhesion and polarization of macrophages, the method including controlling cell adhesion and polarization of macrophages by treating the nanohelix-substrate complex for controlling cell adhesion and polarization of the macrophages with a culture medium and then applying a magnetic field in a range from 20 mT to 7 T, and in which a length of the nanohelix is reversibly changed depending on application/non-application of a magnetic field, and the length of the nanohelix satisfies Equation 1 below.

$$|L_1-L_0|>10 \text{ nm} \qquad \text{[Equation 1]}$$

In Equation 1, $L_1$ is a length of the nanohelix when a magnetic field is applied, and $L_0$ is a length of the nanohelix when a magnetic field is not applied.

In the controlling of the cell adhesion and the polarization of the macrophages, it is possible to control adhesion and polarization of macrophages in vivo and ex vivo by reversibly changing the length of the nanohelix depending on application/non-application of the magnetic field to the nanohelix-substrate complex.

In particular, in the controlling of the adhesion and the polarization of the macrophages, when the magnetic field is not applied to the nanohelix-substrate complex, the nanohelix is compressed and a pitch interval of the nanohelix is decreased to promote an inflammatory (M1) phenotype.

Further, in the controlling of the cell adhesion and the polarization of the macrophages, when the magnetic field is applied to the nanohelix-substrate complex, the nanohelix is stretched and a pitch interval of the nanohelix is increased to promote a regenerative and anti-inflammatory (M2) phenotype.

For example, when the magnetic field is applied to the nanohelix-substrate complex and then the magnetic field is removed, the nanohelix is reversibly stretched and compressed.

Accordingly, it is possible to temporally and reversibly control the cell adhesion and polarization of macrophages by using the nanohelix-substrate according to the present invention.

In particular, in Equation 1, it can be seen that a change in the length of the nanohelix depending on application/non-application of the magnetic field may be 10 nm or more, 20 nm or more, 10 nm to 500 nm, or 10 nm to 100 nm.

When the change in the length of the nanohelix in the nanohelix-substrate complex of the present invention does not satisfy Equation 1, the change in the length of the nanohelix is small, so there is no difference in cell adhesion performance, which is a problem.

Hereinafter, examples of the present invention will be described. However, the examples below are merely preferable examples of the present invention, and the scope of the present invention is not limited by the examples.

Preparation Example

Preparation Example
Prepare Nanohelix

A nanohelix was prepared by using an AAO porous template having pores with 200 nm in diameter through electrodeposition. First, silver (Ag) was deposited on one surface of the AAO porous template by using an electron-beam evaporator. A metal ion precursor solution was prepared by mixing cobalt sulfate heptahydrate ($CoSO_4.7H_2O$, 0.08M) and iron sulfate heptahydrate ($FeSO_4.7H_2O$, 0.08M) in deionized water. In order to produce CoFe nanohelices, vanadium (IV) oxide sulfate ($VOSO_4.xH_2O$), and L-ascorbic acid (0.06 M) were added to the metal ion precursor solution. Next, nitric acid was then added to the precursor solution to adjust the pH to 2.5, the mixed precursor solution was injected into the pores of the AAO template pores, and then a current at constant current density of 20 $mA/cm^2$ was applied to deposit CoFe nanohelices. The nanotemplate was removed by reacting the CoFe nanohelix-deposited nanotemplate and 1 M of NaOH for 30 minutes at 45° C., followed by washing the CoFe nanohelix with deionized water to prepare the CoFe nanohelices. The washed CoFe nanohelices were suspended in 1 mL of deionized water before being coupled to the substrate.

Comparative Preparation Example

A nanohelix was prepared by the same method as that of Preparation Example 1 except that a negatively charged thiolated RGD peptide (CDDRGD, GL Biochem) was not added.

EXAMPLE

Example
Prepare Nanohelix-Substrate Complex

Aminocaproic acid was used to be coupled to a surface of a magnetic CoFe nanohelices based on an amine group that is reported to react with the native oxide layer of the nanohelices prepared in the preparation example. A mixed solution of 1 mL of nanohelices and 1 mL of 6 mM of an aminocaproic acid solution were stirred at a room temperature for 12 hours, and then centrifuged and washed with deionized water. A cell culture grade glass substrate (22 mm×22 mm) was aminated to allow a carboxylate group on the surface of the nanohelix to be bonded to the amine group on the substrate. The substrate was first washed with a mixture in which hydrochloric acid and methanol were mixed at a ratio of 1:1 for 30 minutes and rinsed with deionized water. The washed substrate was activated in sulfuric acid for 1 hour and washed with deionized water. The substrate was aminated in 3-aminopropyl triethoxy silane (APTES) and ethanol (1:1) in a darkroom for 1 hour and washed with ethanol, followed by drying for 1 hour at 100° C. The aminocaproic acid-conjugated nanohelices were activated in 1 mL of deionized water containing 0.5 mL of 20 mM N-ethyl-N'-(3-(dimethylaminopropyl)carbodiimide) (EDC) and 0.5 mL of 20 mM N-hydroxysuccinimide (NHS) through EDC/NHS reaction for 3 hours, followed by washing with deionized water. The aminated substrate was incubated with the activated nanohelices for 1 hour, followed by washing with deionized water. An integrin ligand was cultured in 1 mL of deionized water containing 0.04 mM of maleimide-poly(ethylene glycol)-NHS linker and 2 µl of N,N-Diisopropylethylamine (DIPEA, 2 µL) under the shaking in the dark for 16 hours, grafted on the surface of the substrate by mediating the amide bond formation, followed by washing with deionized water. To mediate the thiol-ene reaction, the substrate was cultured in 1 mL of deionized water containing thiolated RGD peptide ligands (GCGYGRGDSPG, GL Biochem, 0.04 M), 2 µL of N,N-diisopropylethylamine (DIPEA), and 10 mM Tris(2-carboxyethyl)phosphine hydrochloride (TCEP) for 2 hours in the dark, and then washed with deionized water. To minimize the non-RGD ligand specific macrophage adhesion before the culturing of the cell, the areas to which the nanohelix was not coupled were activated in 1 mL of deionized water containing 2 µL of N,N-diisopropylethylamine (DIPEA) and 100 µM methoxy-poly(ethylene glycol)-succinimidyl carboxymethyl ester in the dark for 2 hours, followed by washing to block the non-nanohelix-coated area of the substrate.

Comparative Example 1

A nanohelix-substrate complex was prepared by the same method except for using the prepared nanohelix Comparative Preparation Example 1.

EXPERIMENTAL EXAMPLE

Experimental Example 1

In order to check the form and the chemical characteristic of the nanohelix according to the present invention, the prepared nanohelices were photographed by using a Scanning Electron Microscope (SEM), a High-Angle Annular Dark-Field Scanning Transmission Electron Microscopy (HAADF-STEM), a High-Resolution Transmission Electron Microscope (HR-TEM), and a High-Resolution Scanning Transmission Electron Microscopy (HR-STEM), and then analyzed by using Energy Dispersive X-ray Spectroscopy (EDS), Electron Energy Loss Spectroscopy (EELS), Vibrating-Sample Magnetometry (VSM), and X-ray Diffraction (XRD), and a result thereof is represented in FIGS. 2 and 7.

FIG. 2 is an SEM image of the nanohelix according to the present invention. In particular, an upper left part of FIG. 2 is an SEM image of the CoFe nanohelix prepared by regulating a pore diameter of an electrodeposition template, an upper right part of FIG. 2 is an SEM image of cobalt nanohelices and the CoFe nanohelices, and a lower part of FIG. 2 is an SEM image of the measured length of the CoFe nanohelix according to an electrodeposition time, and in this case, a scale bar represents 500 nm in the upper left part of FIG. 2, 200 nm in the upper right part of FIG. 2, and 1 μm in the lower part of FIG. 2.

Referring to FIG. 2, according to the nanohelix according to the present invention, it can be seen that it is possible to regulate the diameter of the CoFe nanohelix according to the pore diameter of the electrodeposition template, it is possible to control a constituent element of the nanohelix according to the control of the metal ion precursor, and it is possible to regulate the length of the CoFe nanohelix according to an electrodeposition time.

FIG. 3 is an HAADF-STEM image, an EDS mapping image, and an HR-STEM image of the nanohelix according to the present invention.

FIG. 4A is a graph illustrating an EDS analysis result and FIG. 4B is a graph illustrating an EELS analysis result of the nanohelix according to the present invention.

Referring to FIGS. 3 and 4, in the HAADF-STEM image, it can be seen that the nanohelix consists of cobalt (Co) and iron (Fe), each of which is constantly distributed with a distribution of about 50 atom %.

FIG. 5 is a graph illustrating a measurement result of a vibrating-sample magnetometry of the nanohelix according to the present invention. In particular, the magnetic characteristic of the nanohelix by cobalt and iron was confirmed, and through this, it can be recognized that reversible bimodal switching between nano stretching ("ON") and nano-compression ("OFF") of the nanohelix is possible.

FIG. 6 is an X-ray diffraction analysis graph of the nanohelix according to the present invention, and FIG. 7 is an HRTEM image of the nanohelix according to the present invention.

Referring to FIGS. 6 and 7, it can be seen that the nanohelix has a (110) crystalline plane of a body-centered cubic structure, and has an average lattice interval of about 2.02±0.02 Å. Further, it can be seen that in order to promote the coupling with the isotropic integrin ligand, the diameter of the nanowire forming the nanohelix is almost similar to about 10 nm that is an integrin molecule size.

Experimental Example 2

In order to confirm the characteristic of the nanohelix-substrate complex according to the present invention, the nanohelix-substrate complex was photographed with a Field Emission Scanning Electron Microscope (FE-SEM), the Fourier-Transform Infrared Spectroscopy (FT-IR) was carried, and the nanohelix-substrate complex was photographed with an Atomic Force Microscope (AFM), and the results thereof are represented in FIGS. 8 to 11.

The FT-IR was conducted by using GX1 (Perkin Elmer Spectrum, USA) in order to confirm the chemical bond characteristics of the nanohelices. The samples analyzed for the change in chemical bond characteristics were lyophilized and densely packed into KBr pellet prior to the analysis.

FIG. 8 is an image schematically illustrating an operation of preparing the nanohelix-substrate complex according to the present invention. Referring to FIG. 8, aminocaproic acid was coupled to the nanohelix. Next, the aminocaproic acid-bonded nanohelix was put in water containing EDC and NHS and activated by using the EDC/NHS reaction, and then was coupled to the substrate of which the surface is aminated. Polyethylene glycol was coupled to aminocaproic acid coupled to the nanohelix that is not coupled with the substrate, and the integrin ligand was coupled to the nanohelix by reacting the polyethylene glycol and the thiolated integrin ligand (RGD).

FIG. 9 is a diagram illustrating an FT-IR analysis result of the nanohelix-substrate complex according to the present invention. Referring to FIG. 9, the chemical bond characteristics of the aminocaproic acid-coated nanohelix can be recognized. In particular, $COO^-$ binding was confirmed at 1560-1565 $cm^{-1}$ and 1387-1389 $cm^{-1}$. Through this, it can be seen that aminocaproic acid was successfully coupled to the nanohelix.

In addition, in order to minimize adhesion of non-ligand-specific macrophages, the substrate that is not coupled with the nanohelix was coupled with a methoxy-PEG-NHS ester group to be inactivated, and referring to FIG. 3, the uniform distribution of the nanohelices can be confirmed through the scanning electron microscope, and it can be seen that a density of the nanohelices is about 62802±2385 nanohelices/$mm^2$.

FIG. 10 is a diagram illustrating the result obtained by using the AFM in order to confirm magnetic bimodal switching of an elastic motion with stretching ("ON") and compression ("OFF") of the nanohelix according to the present invention. FIG. 11 is a diagram illustrating the result obtained by photographing the case where a magnetic field is not applied to the nanohelix according to the present invention by using the AFM.

Referring to FIGS. 10 and 11, it can be seen that in the nanohelix-substrate complex according to the present invention, when a magnetic field is applied, the nanohelix is stretched, so that the length of the nanohelix increases, and when the magnetic field is not applied again, the nanohelix is compressed, so that the length of the nanohelix returns to the original state. However, it can be seen that only the length of the nanohelix is simply increased and then decreased again, but the outer diameter of the nanohelix or the diameter of the nanowire forming the nanohelix is not significantly different.

In particular, it can be seen that the length of the nanohelix before the application of the magnetic field is 1060±9 nm and the length of the nanohelix when the magnetic field is applied is 1243±25 nm, and when the magnetic field is not applied again, the length of the nanohelix is decreased to 1052±9 nm. In this case, the diameter of the nanohelix is maintained with 174 nm to 181 nm, and the diameter of the nanowire forming the nanohelix is maintained with 83 to 86 nm, so that it can be seen that the outer helix diameter and the wire diameter of the nanohelix remained similar without significant differences during the cyclic switching "OFF", "ON", and "OFF".

Through this, it can be seen that in the nanohelix-substrate complex of the present invention, the macroscale ligand density is constantly maintained during the bimodal switching.

Experimental Example 3

The following experiment was conducted to confirm an influence on the adhesion of macrophages according to the application of a magnetic field to the nanohelix-substrate complex according to the present invention, and the result thereof is represented in FIGS. 12 to 15.

The effect of controlling adhesion and phenotypic polarization of macrophages under the bimodal switching of the nanohelix was accessed. The substrate was subjected to sterilization under ultraviolet light for 2 hours prior to the culture. Macrophages (RAW 264.7, passage 5, ATCC) were seeded onto the sterilized substrate at the density of about $9 \times 10^4$ cells/$cm^2$, and were cultured under basal growth medium containing high glucose Dulbecco's Modified Eagle Medium (DMEM) with 10% heat-inactivated fetal bovine serum, and 50 IU/mL penicillin and streptomycin antibiotics at 37° C. under 5% $CO_2$. Bimodal switching-regulated adhesion of macrophages was accessed under cyclic switching between "ON" state (placing a permanent magnet (270 mT) near the edge of the substrates, in which the ligand-bearing nanohelices were stretched toward the edge of substrates) and "OFF" state (withdrawing the magnet from the substrate, in which the ligand-bearing nanohelices were compressed to revert to their original nanostructures). Control experiments to assess macrophage adhesion were conducted under bimodal switching, but were conducted in the absence of the nanohelices or integrin ligands.

M1 medium used for assessment of the phenotypic polarization of macrophages was prepared by using a basal medium with 10 ng/mL each of lipopolysaccharide (LPS) and recombinant interferon-gamma (IFN-γ). M2 medium was prepared by using a basal medium with 20 ng/mL each of interleukin-4 (IL4) and interleukin-13 (IL-13). The adhesion-assisted M2 phenotypic polarization of the macrophages was assessed with inhibitors of ROCK (50 μM Y27632), myosin II (10 μM blebbistatin), or actin polymerization (2 μg/mL of cytochalasin D).

FIG. 12 is a confocal immunofluorescent image of F-actin, nuclei, and vinculin in macrophages cultured (for 24 hours) by using the nanohelix-substrate complex according to the present invention (upper part), and a graph illustrating a cell density, a cell area, and a cell elongation factor calculated based on the result of the confocal immunofluorescent experiment (lower part), and a scale bar indicates 20 μm.

Referring to FIG. 12, in the confocal immunofluorescent image, the macrophages have considerably larger cell adhesion density and vinculin and F-actin spread areas in the "ON" mode in which a magnetic field is applied in the bimodal switching, compared to the "OFF" mode in which a magnetic field is not applied, which shows the adhesion of macrophages was promoted when the magnetic field is applied.

Through this, it was confirmed that the macroscale stretching-mediated macrophage adhesion may exhibit nanoscale stretching to promote the macrophage adhesion.

FIG. 13 is a confocal immunofluorescent image for live cells and dead cells of macrophages cultured (for 24 hours) by using the nanohelix-substrate complex according to the present invention (upper part), and a graph illustrating cell viability calculated based on the result of the confocal immunofluorescent experiment (lower part), and a scale bar represents 50 μm.

Referring to FIG. 13, it can be seen that even in the bimodal switching in which the magnetic field is applied, cell viability is excellent at 95%, so that the nanohelix-substrate complex has excellent cellular compatibility for macrophages.

FIG. 14 is a diagram illustrating a result of an experiment for adhesion of macrophages for bimodal switching in a substrate having no nanohelix or the nanohelix-substrate complex to which the integrin ligand (RGD) is not coupled according to a comparative example of the present invention, and an upper part of FIG. 14 is a confocal immunofluorescent image of F-actin, nuclei, and vinculin in macrophages cultured for 24 hours, and a lower part of FIG. 14 is a graph representing a cell density, a cell area, and a cell elongation factor calculated based on the confocal immunofluorescent experiment result, and in this case, a scale bar represents 20 μm.

Referring to FIG. 14, in the comparative example, there is no significant difference in the bimodal switching "ON" and "OFF" in the state of using the substrate having no nanohelix or the substrate to which the integrin ligand (RGD) is not coupled, so that the adhesion of macrophages is not promoted.

Through this, in the case of the nanohelix-substrate complex of the present invention, it can be seen that the bimodal switching exhibits an effect only when the integrin ligand is coupled to the nanohelix.

FIG. 15 is a confocal immunofluorescent image of F-actin, nuclei, and vinculin in macrophages cultured for 36 hours by regulating application of a magnetic field at an interval of 12 hours by using the nanohelix-substrate complex according to the present invention, and a scale bar represents 20 μm.

Referring to FIG. 15, it can be seen that in the case where a magnetic field is not applied, there is no change in cell adhesion, and in the case where a magnetic field is applied, cell adhesion is promoted, and in the case where a magnetic field is not applied again, cell adhesion is reversibly decreased.

Through this, the nanohelix-substrate complex of the present invention temporally and reversibly promotes and suppresses the adhesion of macrophages through the stretch and the compression of the nanohelix.

Experimental Example 4

An experiment on the control of the nano-periodicity controls phenotypic polarization-mediated adhesion of macrophages by using the nanohelix-substrate complex according to the present invention was performed as described below, and the result thereof is represented in FIGS. 16 to 22.

The adhesive structures of macrophages are known to modulate their phenotypic polarization in the presence of M1 or M2 polarization stimulators. In particular, macrophages that develop robust adhesion structures, including the assembly of prevalent F-actin and vinculin in elongated shapes, are prone to activate their phenotypic polarization into regenerative/anti-inflammatory M2 state. In contrast, macrophages with low F-actin and rounded shape are prone to activate the M1 state.

FIG. 16 is a result of an experiment for control of macrophage adhesion-dependent phenotypic polarization of macrophages by application of a magnetic field by using the nanohelix-substrate complex according to the present invention.

Referring to FIG. 16, immunofluorescent confocal images revealed that macrophages gradually exhibited weaker CD68 fluorescence signals in M1-induction medium as a magnetic field is applied, but exhibited stronger Arg-1 fluorescence signals in M2-induction medium as a magnetic field is applied. Further, it can be seen that gene expression profiles were prone to be observed in the immunofluorescence. The macrophage exhibited the considerably low iNOS and TNF-α expression in the M1-induction medium as a magnetic field is applied, but exhibited high Arg-1 and Ym1 expression in the M2-induction medium as a magnetic field is applied.

Through this, it can be seen that the bimodal switching of the nanohelix controlling macrophage adhesion according to the application of the magnetic field may control polarization dependent on adhesion of macrophages.

FIG. 17 is a result of an experiment for controlling application of a magnetic field when there is no stimulation medium matched to a polarization phenotype (that is, M1 expression in an M2-stimulation medium or M2 expression in an M1-stimulation medium) by using the nanohelix-substrate complex according to the present invention.

Referring to FIG. 17, it was found that the controlling of the application/non-application of the magnetic field under no presence of the stimulation medium matched with the polarization phenotype (that is, M1 expression in the M2-stimulation medium or M2 expression in the M1-stimulation medium) did not exhibit a meaningful difference in iNOS, TNF-α, Arg-1, and Ym1 expression.

Through this, it can be seen that M1 and M2 stimulation does not affect the change in M1 or M2 expression without appropriate stimulation, respectively.

FIG. 18 is a confocal immunofluorescent image of ROCK2 and nuclei after macrophages are cultured in an M1 or M2 medium under bimodal switching of stretching ("ON") in which a magnetic field is applied and compression ("OFF") in which a magnetic field is not applied for 36 hours (upper part), and a graph illustrating ROCK2 immunofluorescent intensity calculated based on a result of the confocal immunofluorescent experiment (lower part), and a scale bar represents 20 μm.

Referring to FIG. 18, it can be seen that the application of the magnetic field elevated ROCK2 expression under M2 medium culture compared to the non-application of the magnetic field. Through this, the adhesion-dependent M2 polarization of macrophages is mediated by the stretching ("ON") condition in which the magnetic field is applied.

An upper part of FIG. 19 is a confocal immunofluorescent image of CD68, F-actin, and nuclei in macrophages cultured in an M1 polarization medium with and without an inhibitor for ROCK (Y27632), myosin II (blebbistatin), or actin polymerization (cytochalasin D) for 36 hours against and a graph illustrating a cell area, a cell elongation factor, and CD68 fluorescence intensity calculated based on a confocal immunofluorescent experiment result, and a lower part of FIG. 19 is a confocal immunofluorescent image of Arg-1, and F-actin, and nuclei in macrophages cultured in an M2 polarization medium with and without an inhibitor for ROCK (Y27632), myosin II (blebbistatin), or actin polymerization (cytochalasin D) and a graph illustrating a cell area, a cell elongation factor, and Arg-1 fluorescence intensity calculated based on the confocal immunofluorescent experiment result, and a scale bar represents 20 μm.

Referring to FIG. 19, it can be seen that under the M1 medium culture using pharmacological inhibitors (Y27632, blebbistatin, or cytochalasin D) that inhibit ROCK, myosin II, or actin polymerization, the M1 polarization suppression of macrophages is continuously hindered under the bimodal switching "ON" state. Further, it can be seen that under the M2 medium culture, when the inhibitor is treated, stimulation of robust adhesion (higher cell area and elongation factor) and expression of M2 polarization (Arg-1 expression) are hindered.

Through this, ROCK, myosin II, and F-actin function as molecular switches in the regulation of bimodal M1 vs. M2 polarization in concert with the magnetic bimodal switching of the integrin ligand-bearing nanohelices.

Experimental Example 5

A following experiment was conducted in order to confirm the spatial control of adhesion and phenotype of host macrophages in vivo through stretching and compression of the nanohelix according to the application of a magnetic field by using the nanohelix-presenting substrate according to the present invention, and a result thereof is presented in FIGS. 20 to 22.

FIG. 20 is a diagram illustrating a result of an experiment for control of adhesion and phenotype of host macrophages in vivo by using the nanohelix-substrate complex according to the present invention. An upper part of FIG. 20 is a schematic diagram illustrating the case where a magnetic field is applied to the nanohelix-substrate complex in vivo, and in this case, both interleukin-4 and interleukin-13 (M2 inducing agent) were injected onto the subcutaneous implanted substrate in vivo. A middle part of FIG. 20 is a confocal immunofluorescent image of iNOS, F-actin, and nuclei in host macrophage adhered to the substrate after 24 hours under the bimodal switching of stretching ("ON") and compression ("OFF") of the nanohelix and a quantitative graph thereof, and a scale bar represents 20 μm. A lower part of FIG. 20 is a graph of a quantitative analysis result of the adherent host macrophage in vivo of M1 phenotypic marker (iNOS and TNF-α) adhered to the substrate after 24 hours under the bimodal switching of stretching ("ON") and compression ("OFF") of the nanohelix.

An upper part of FIG. 21 is a confocal immunofluorescent image of Arg-a, F-actin, and nuclei in host macrophage adhered to the substrate after 24 hours under the bimodal switching of stretching ("ON") and compression ("OFF") of the nanohelix, and a scale bar represents 20 μm. A lower part of FIG. 21 is a graph of a quantitative analysis result of the adherent host macrophage in vivo of M2 phenotypic marker (Arg-1 and Ym1) adhered to the substrate after 24 hours under the bimodal switching of stretching ("ON") and compression ("OFF") of the nanohelix.

FIG. 22 is a diagram illustrating a result of an experiment of adhesion in vivo of host neutrophil to the substrate by using the nanohelix-substrate complex according to the present invention. An upper part of FIG. 22 is an immunofluorescent confocal image of NIMP-R14, F-actin, and the nuclei in host macrophages adhered to the substrate after 24 hours, and in this case, a scale bar represents 20 μm. A lower part of FIG. 22 is a graph of quantification data of in vivo adherent NIMP-R14-positive host neutrophils, and both interleukin-4 and interleukin-13 were injected onto the subcutaneously implanted substrate coupled with the nanohelix.

Referring to FIGS. 20 to 22, it can be seen that the stretching ("ON") in which a magnetic field is applied in the bimodal switching exhibits significantly higher adherent cell density, F-actin spread area, more pronounced elongation, and low iNOS and TNF-α expression, compared to the compression "OFF") in which a magnetic field is not applied to promote time-regulated adhesion that inhibits M1 polarization of host macrophages. Further, it can be seen that the stretching ("ON") in which a magnetic field is applied in the bimodal switching has a robust adherent structure, and temporarily stimulates adhesion-mediated M2 polarization of host macrophages exhibiting significantly high Arg-1 and Ym1 expression associated with adherent NIMP-R14 positive neutrophils, compared to the compression ("OFF") in which a magnetic field is not applied.

What is claimed is:

1. A metallic nanohelix-substrate complex for controlling adhesion and polarization of macrophages, the metallic nanohelix-substrate complex comprising:
   a substrate;
   one or more metallic nanohelices chemically coupled to the substrate; and
   one or more integrin ligand peptides chemically coupled to the one or more metallic nanohelices, wherein the one or more metallic nanohelices are formed of a spiral nanowire and comprise one or more metal elements selected from the group consisting of cobalt (Co), iron (Fe), and nickel (Ni), the one or more metallic nanohelices have a length of 100 nm to 20 μm, and the one or more metallic nanohelices have a length reversibly changed depending on application/non-application of a magnetic field within a range of Equation 1 below, $$|L_1-L_0|>10 \text{ nm} \quad \text{[Equation 1]}$$

in Equation 1, $L_1$ is a length of the one or more metallic nanohelices when the magnetic field is applied, and $L_0$ is a length of the one or more metallic nanohelices when the magnetic field is not applied, wherein the one or more integrin ligand peptides comprise a thiolated integrin ligand peptide, and wherein a thiol group of the thiolated integrin ligand peptide is coupled to the spiral nanowire by a polyethylene glycol linker.

2. The metallic nanohelix-substrate complex of claim 1, wherein the spiral nanowire is provided in a form of a metallic wire having a circular cross-section, and has a diameter of 5 nm to 100 nm, and wherein an average length of a spiral outer diameter of the one or more metallic nanohelices is 50 nm to 200 nm.

3. The metallic nanohelix-substrate complex of claim 1, wherein the applied magnetic field has a magnitude of 100 mT to 7 T.

4. The metallic nanohelix-substrate complex of claim 1, wherein the one or more integrin ligand peptides are coupled to the one or more metallic nanohelices while being spaced apart from each other, and an average interval between adjacent integrin ligand peptides is 1 nm to 10 nm.

5. The metallic nanohelix-substrate complex of claim 1, wherein when the magnetic field is applied, adjacent spirals of the one or more metallic nanohelices are spaced apart from each other, and a pitch between the adjacent spirals is 1 nm to 100 nm.

6. The metallic nanohelix-substrate complex of claim 1, wherein the one or more metallic nanohelices are coupled to the substrate by coupling carboxylate to the one or more metallic nanohelices.

7. The metallic nanohelix-substrate complex of claim 1, wherein a surface of the substrate, which is not coupled with the one or more metallic nanohelices, is inactivated by being coupled with a methoxy-PEG-NHS ester group.

8. A method of preparing the metallic nanohelix-substrate complex of claim 1, the method comprising:

preparing the one or more metallic nanohelices by electrodepositing a solution including the one or more metal elements;

coupling a carboxylate substituent to the one or more metallic nanohelices by mixing the one or more nanohelices and a first suspension;

manufacturing the substrate coupled with the one or more metallic nanohelices by soaking a substrate of which a surface is activated in a solution containing the one or more metallic nanohelices to which the carboxylate substituent is coupled;

coupling a linker to a distal end of the one or more metallic nanohelices by soaking the substrate coupled with the one or more metallic nanohelices in a solution containing a polyethylene glycol linker; and coupling the one or more integrin ligand peptides (RGD)—to the one or more nanohelices by mixing a second suspension containing the one or more integrin ligand peptides (RGD) and the activated substrate coupled with the one or more metallic nanohelices.

9. The method of claim 8, wherein in the coupling of the carboxylate substituent, the first suspension includes an amino acid derivative containing the carboxylate substituent, and the amino acid derivative is coupled to a surface of the one or more metallic nanohelices.

10. The method of claim 8, wherein in the coupling of the one or more integrin ligand peptides, the second suspension includes thiolated integrin ligand peptide.

11. The method of claim 8, wherein the manufacturing of the substrate coupled with the one or more metallic nanohelices uses the substrate, of which the surface is aminated by activating a surface of the substrate by immersing the substrate in an acid solution and then soaking the substrate in an aminosilane solution.

12. The method of claim 8, further comprising:

after the coupling of the one or more integrin ligand peptides to the one or more metallic nanohelices, soaking the substrate coupled with the one or more metallic nanohelices in a solution including a polyethylene glycol derivative.

* * * * *